(12) United States Patent
Helgesson et al.

(10) Patent No.: US 6,892,728 B2
(45) Date of Patent: May 17, 2005

(54) INHALATION DEVICE

(75) Inventors: Per Helgesson, Lund (SE); Douglas Jennings, Royston (GB); Craig Nelson, Baldock (GB)

(73) Assignee: AstraZeneca AB, Sodertalje (SE)

( * ) Notice: Subject to any disclaimer, the term of this patent is extended or adjusted under 35 U.S.C. 154(b) by 56 days.

(21) Appl. No.: 10/221,958

(22) PCT Filed: Mar. 21, 2001

(86) PCT No.: PCT/SE01/00601

§ 371 (c)(1),
(2), (4) Date: Oct. 22, 2002

(87) PCT Pub. No.: WO01/70318

PCT Pub. Date: Sep. 27, 2001

(65) Prior Publication Data

US 2003/0075175 A1 Apr. 24, 2003

(30) Foreign Application Priority Data

Mar. 21, 2000 (SE) .............................................. 0000935

(51) Int. Cl.[7] .......................................... A61M 15/00
(52) U.S. Cl. ........................... 128/203.15; 128/203.23; 128/200.22
(58) Field of Search ....................... 128/200.19, 200.23, 128/203.15, 203.23, 200.14, 205.16, 200.22

(56) References Cited

U.S. PATENT DOCUMENTS

| | | | | |
|---|---|---|---|---|
| 6,098,618 A | * | 8/2000 | Jennings et al. ....... | 128/203.15 |
| 6,286,506 B1 | * | 9/2001 | MacAndrew et al. .. | 128/203.15 |
| 6,418,924 B1 | * | 7/2002 | Poley et al. ........... | 128/200.14 |
| 6,557,550 B1 | * | 5/2003 | Clarke ................... | 128/203.15 |

FOREIGN PATENT DOCUMENTS

| WO | WO 97/11732 | | 4/1997 |
|---|---|---|---|
| WO | WO 98/41256 | | 9/1998 |
| WO | WO 98/41263 | * | 9/1998 |

* cited by examiner

*Primary Examiner*—Glenn K. Dawson
*Assistant Examiner*—Darwin P. Erezo
(74) *Attorney, Agent, or Firm*—Fish & Richardson P.C.

(57) ABSTRACT

The present invention relates to an inhalation device for use with an inhaler (5) comprising a dispersion chamber (18) for fluid communication with the inhaler (5) and a suction chamber (19) in fluid communication with the dispersion chamber (18). The suction chamber (19) is constructed to enable the internal volume of the suction chamber (19) to be increased during use thereby producing a negative pressure in the dispersion chamber (18). In this way, the substance to be inhaled can be drawn from the inhaler into the dispersion chamber (18) for subsequent inhalation.

25 Claims, 31 Drawing Sheets

INHALATION DEVICE

CROSS REFERENCE TO RELATED APPLICATIONS

The present application is a national phase application under 35 U.S.C. Section 371 filed from International Patent Application PCT/SE01/00601 filed 21 Mar. 2001, which claims priority to Swedish patent application Serial. No. 0000935-7, filed 21 Mar. 2000. The contents of these applications are incorporated herein by reference in their entirety.

The present invention relates to an inhalation device for inhalation of a pharmaceutically active substance prepared in a dispersed state.

Inhalable pharmaceutically active substances are generally used for the treatment of diseases in the bronchial and pulmonary area, such as asthma and chronic bronchitis. Various types of inhalation devices or apparatus are used for this purpose.

The breath-actuated inhaler is known and used widely, typically containing multiple doses of a medicament containing an active substance. The breath-actuated inhaler usually contains a dry powdered medicament and comprises a manoeuvring element which loads a single dose of the medicament into a dosing unit which can then be inhaled by the user. Inhalers of this kind are described in EP-0,069,715, EP-0,237,507 and WO98/41256, for example.

The inhaler described in the above-mentioned patents is known as the Turbuhaler® inhaler and is particularly advantageous for delivering a dry powdered medicament. The Turbuhaler® inhaler depends on the creation of an airflow through the inhaler which will normally be created by the user inhaling. The airflow will cause the dry powdered medicament to be moved from a release position in the dosing unit into the airflow where it is dispersed and delivered to the mouth of the user. It is important that there is a break down of aggregated particles during inhalation because aggregates always occur in powders having fine particles, especially finely divided particles of the type generally used for inhalation.

The Turbuhaler® inhaler is a manually actuated inhaler intended to be easily carried by the user and actuated when necessary. However, the user must be able to achieve the necessary inhalation flow to move the dry powdered medicament from the release position in the dosing unit into the airflow. Some patients such as small children and elderly people with diseases in the bronchial area are unable to use the breath-actuated inhaler because they simply do not have sufficient lung capacity to create the necessary inhalation flow. The airflow needed is approximately 30 to 60 l/min and patients not having the ability to achieve that airflow must use inhalers which utilise pressurised gas. e.g., freon (CFC) to deliver the medicament. However, pressurised gas inhalers have many disadvantages such as unwanted side effects both for the patient and the environment.

In order to facilitate the use of breath-actuated inhalers, inhalation devices have been developed which make use of a dispersion chamber into which the captive substance is dispersed and then simply inhaled by the patient. Such inhalation devices are described in EP-0,548,152 and WO 97/11732 where the breath-actuated inhaler is inserted into the inhalation device. This type of inhalation device (generally known as a "spacer") is primed for use either by the patient, the nurse or the parent and the patient need only inhale the active substance which has been dispersed in the dispersion chamber. In WO 97/11732, the inhalation device is primed for use by creating a negative pressure in the dispersion chamber which draws out the active substance from the dosing unit within the inhaler. The inhalation device described in WO 97/11732 was designed for use with a breath-actuated inhaler such as the Turbuhaler® inhaler and is operated by lifting the dispersion chamber away from the base and then rotating the dispersion chamber. At the end of the rotational movement, a piston is released which creates the negative pressure in the dispersion chamber. When the dispersion chamber is rotated, the breath-actuated inhaler is held in the inhalation device in such a way that the manoeuvring element in the form of a rotatable gripping part is also rotated. The rotation of the gripping part releases the active substance into the dosing unit. Accordingly, when the piston is released the airflow arising due to the negative pressure in the dispersion chamber will draw out the active substance from the inhaler into the dispersion chamber. The patient is then able to inhale the dispersed substance through a mouthpiece or face mask without having to produce a vigorous intake of breath to create an airflow.

Whilst the spacer described above works effectively, after repeated use the active substance will build up on the interior surfaces of the device which could be dislodged and affect the dose accuracy. Indeed, the build-up of active substance has to be addressed because after a given period, contact with moisture within the device will lead to degradation of the active substance which could be potentially harmful. There is also a demand for an inhalation device which is more compact, more robust and attractive to the patient (who often will have to carry the spacer and use the spacer in a variety of different situations).

A further requirement of the spacer is that it is also able to work with an inhaler of the kind described in WO 98/41256. This version of the Turbuhaler® inhaler is similar to the earlier Turbuhaler® inhaler described in EP 0,069,715 but further comprises a rotating mouthpiece designed to actuate a scraping element which passes over the interior surfaces of the inhaler such that the inhaler can be cleaned prior to each use. With this in mind, there is also a demand for an inhalation device which incorporates a means for rotating the mouthpiece as well as the gripping part of the inhaler.

According to the present invention there is provided an inhalation device for use with an inhaler comprising a dispersion chamber constructed for fluid communication with the inhaler, a suction chamber in fluid communication with the dispersion chamber, the suction chamber being constructed to enable the internal volume of said suction chamber to be increased during use which produces a negative pressure in said dispersion chamber thereby drawing a substance to be inhaled from the inhaler into the dispersion chamber for subsequent inhalation wherein, in use, the dispersion chamber is mounted telescopically around the inhaler.

Preferably, a piston is moveable within the suction chamber.

Preferably, the piston has an annular construction.

Preferably, the piston carries an annular seal member.

Preferably, the annular seal member comprises inner and outer coaxial annular seals.

Preferably, the inhalation device comprises a filter between the dispersion chamber and suction chamber to prevent the dispersed substance from entering the suction chamber.

Preferably, the dispersion chamber is mounted telescopically within the suction chamber.

Preferably, the piston is releasably connected adjacent to and moveable with the dispersion chamber which is moveable between a retracted position, where it surrounds the inhaler, to an extended position, where it sits substantially above the inhaler.

Preferably, there is provided a releasing mechanism for releasing the piston from the dispersion chamber and a biasing means for biasing the piston away from the dispersion chamber when in the extended position and the device is primed for use.

Preferably, when the piston is released the movement of the piston within the suction chamber creates a negative pressure in the dispersion chamber thereby drawing air through the inhaler.

Preferably, the inhalation device comprises a base and a body and is primed for use by lifting the body away from the base and then rotating the base with respect to the body.

Preferably, the dispersion chamber is located in the body and the inhaler is held in the base.

Preferably, the inhaler has a mouthpiece, a body portion and a rotatable gripping part.

Preferably, the inhaler is located within the inhalation device, the rotatable gripping part is held in the base of the inhalation device so that the rotation of the base causes rotation of the rotatable gripping part.

Preferably, the rotation of the gripping part of the inhaler causes the substance to move into a release position within the body portion of the inhaler.

Preferably, the inhaler mouthpiece is rotatable having a scraping means acting on its interior surfaces which cleans the inhaler prior to each use.

Preferably, the inhalation device further comprises a connecting means which links the rotational movement of the gripping part of the inhaler to the rotational movement of the mouthpiece of the inhaler such that rotation of the base in one direction results in the cleaning of the interior surfaces of the inhaler Preferably, the inhalation device further comprises a clamping means which holds the body portion of the inhaler whilst allowing the gripping part to rotate with the base.

Preferably, the body of the inhalation device further comprises a means for drying the air contained within the device and the substance to be inhaled.

Preferably, the body of the inhalation device further comprises a number of separable elements which can be replaced after a predetermined number of uses.

Preferably, the inhalation device comprises a stop element which is configured to ensure that only certain inhalers can be inserted into the device.

Preferably, there is further provided a cover which at least partially encases the inhalation device when not in use.

Preferably, the cover seals and encases the body of the device and connects with the base of the device.

Preferably, the cover and base include parts of an artwork which is only made complete when the user has replaced the cover on the base thereby ensuring that the contents of the inhalation device are sealed within.

Preferably, the inhalation device comprises an audible alarm which is activated after a given period of time should the cover not be replaced.

A preferred embodiment of the present invention will now be described in detail, by way of example only, with reference to the accompanying drawings, of which:

Figure 11:
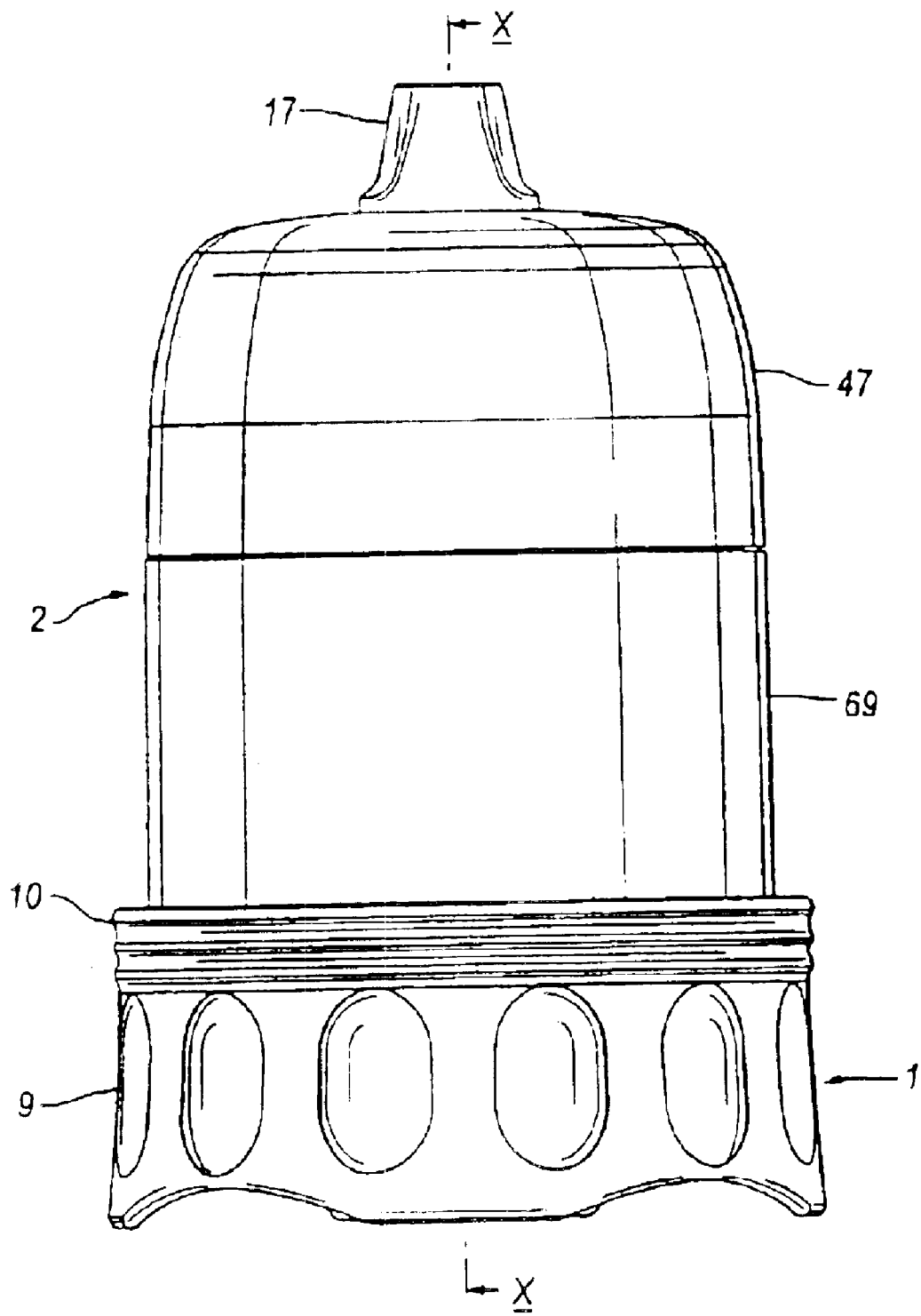
FIG. 11 is a side view of the inhalation device in FIG. 1 with the cover removed and the body in the retracted position.
Figure 12:
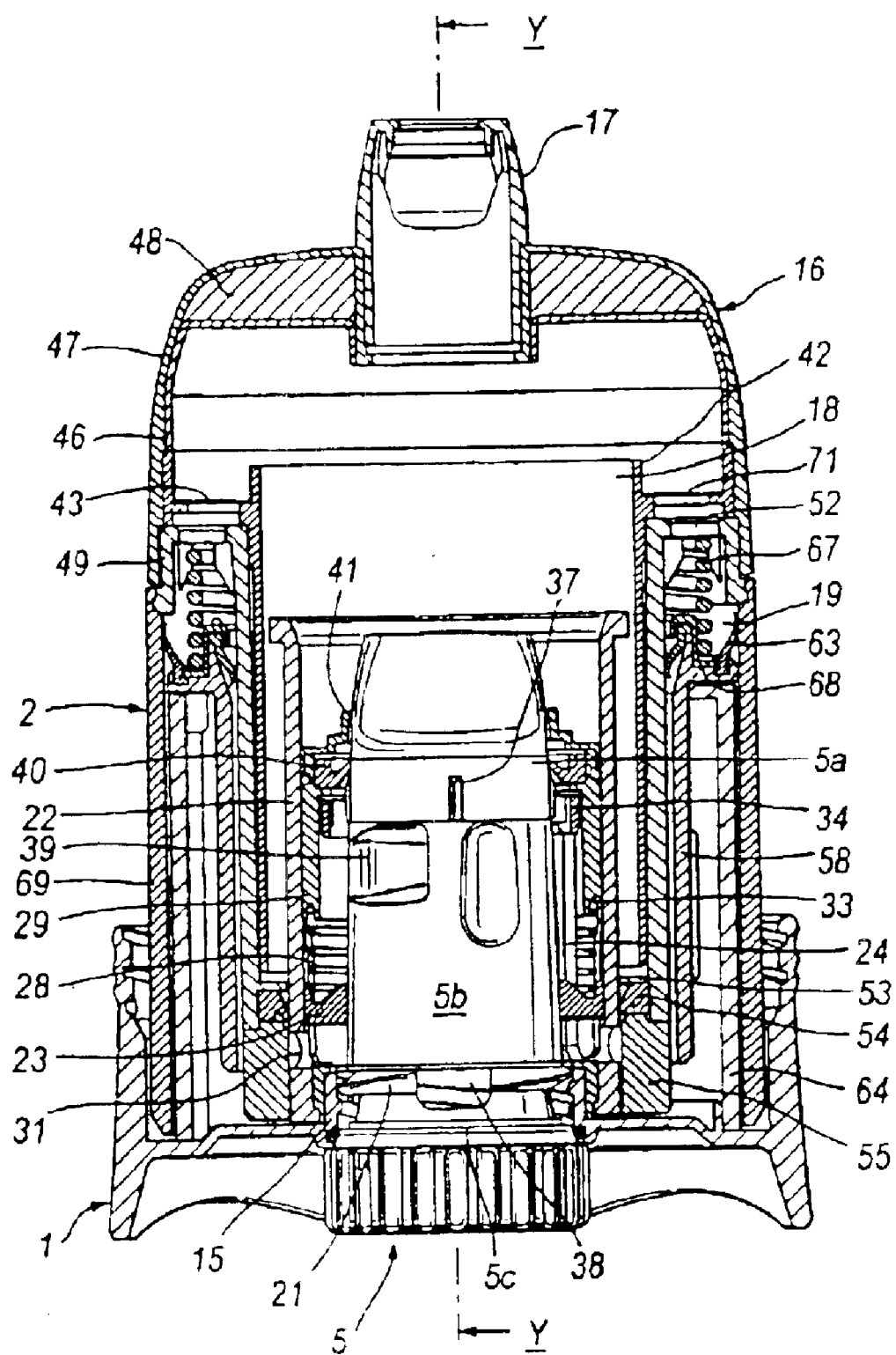
FIG. 12 is a sectional view in direction X—X through the inhalation device in FIG. 11.
Figure 13:
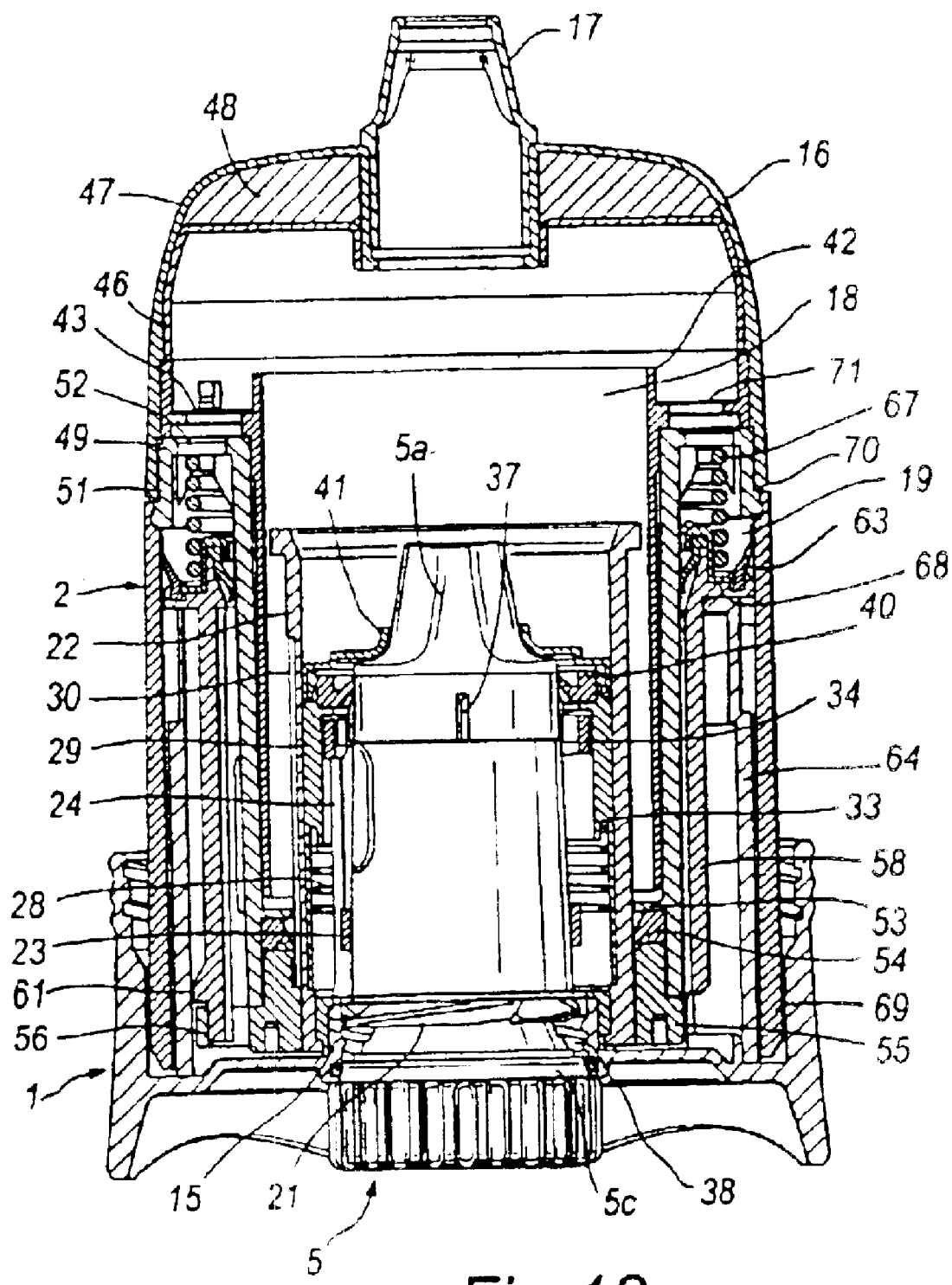
FIG. 13 is a sectional view in direction Y—Y through the inhalation device in FIG. 12.
Figure 14:
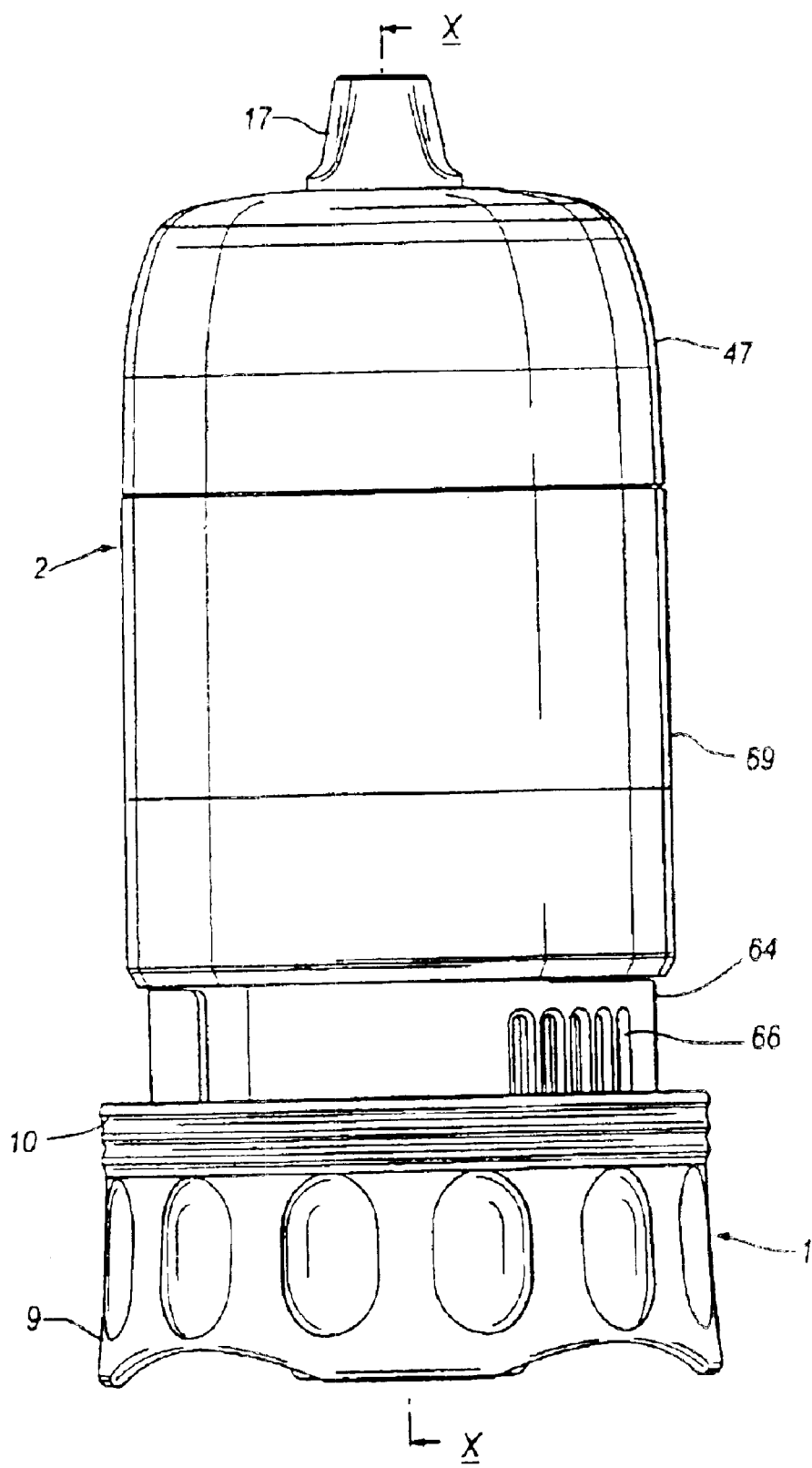
Figure 15:
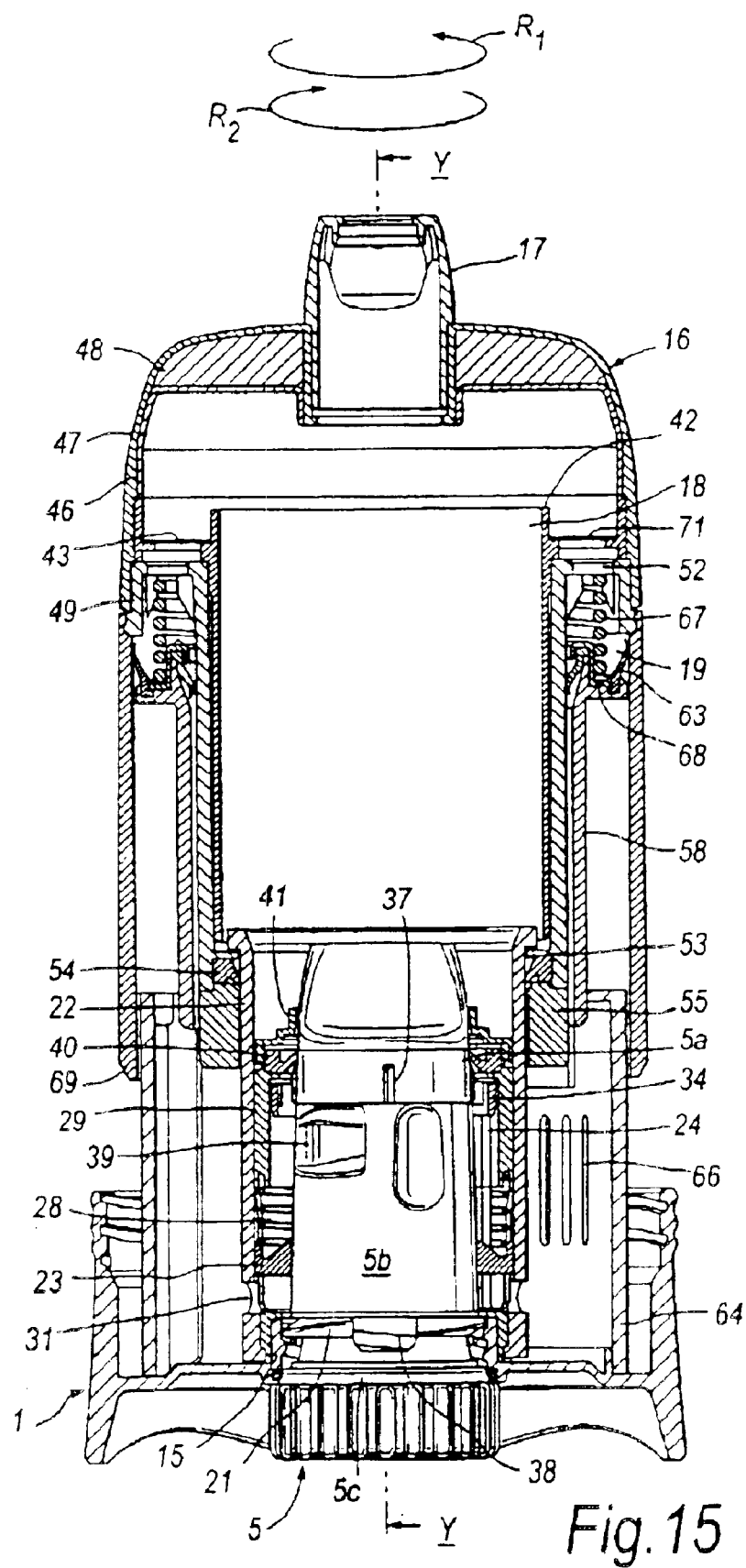
Figure 16:
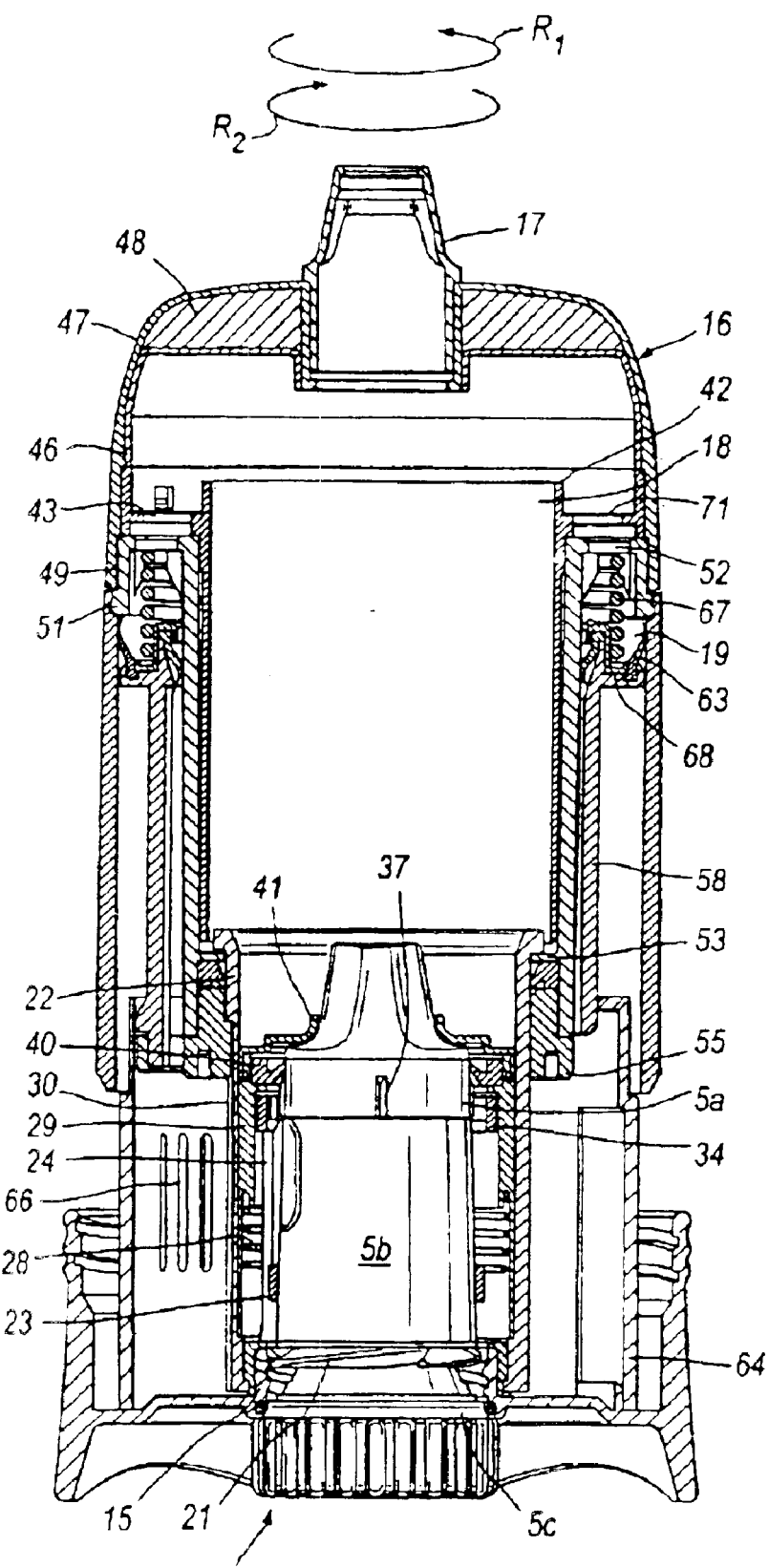
Figure 17:
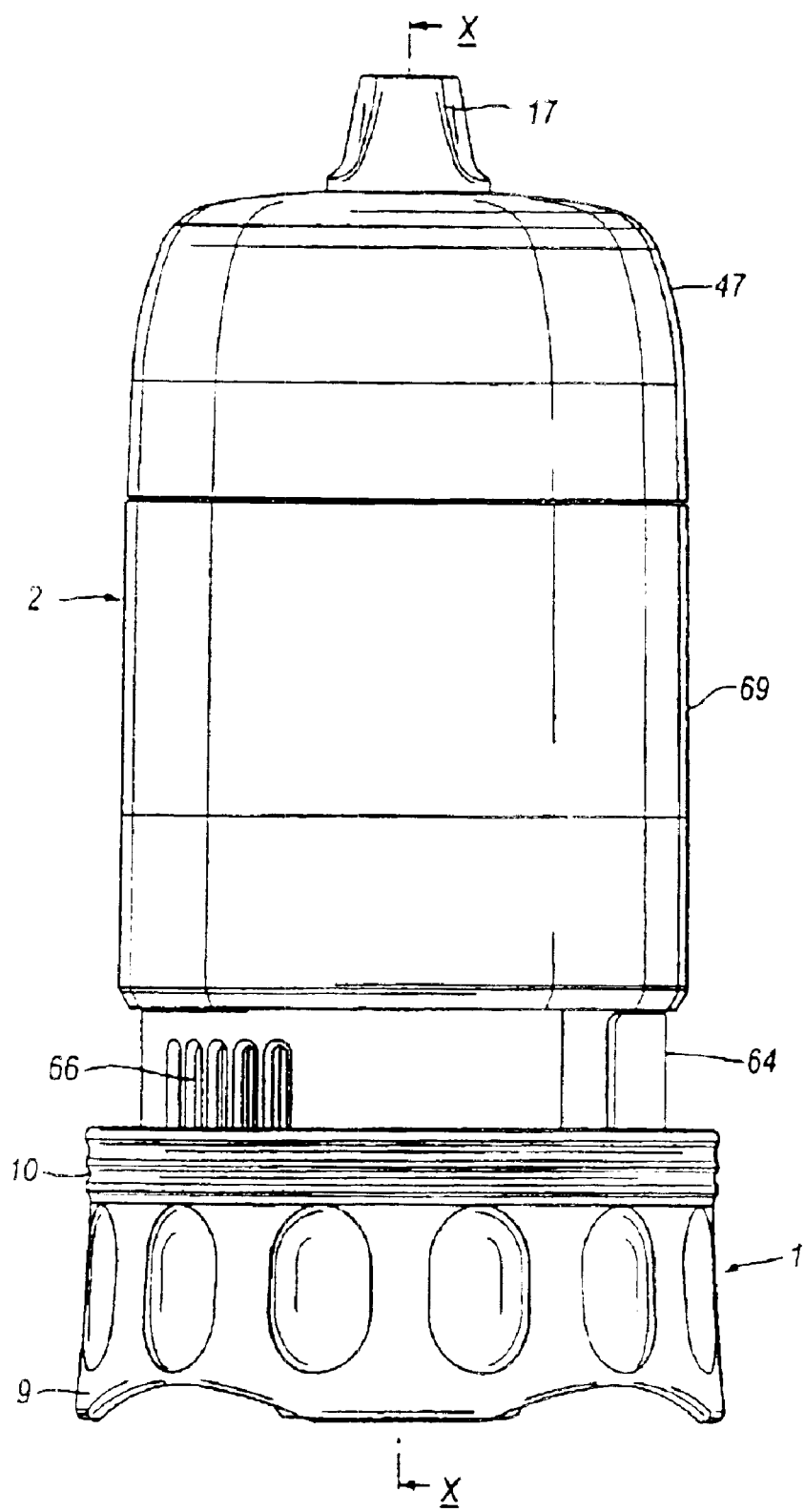
Figure 18:
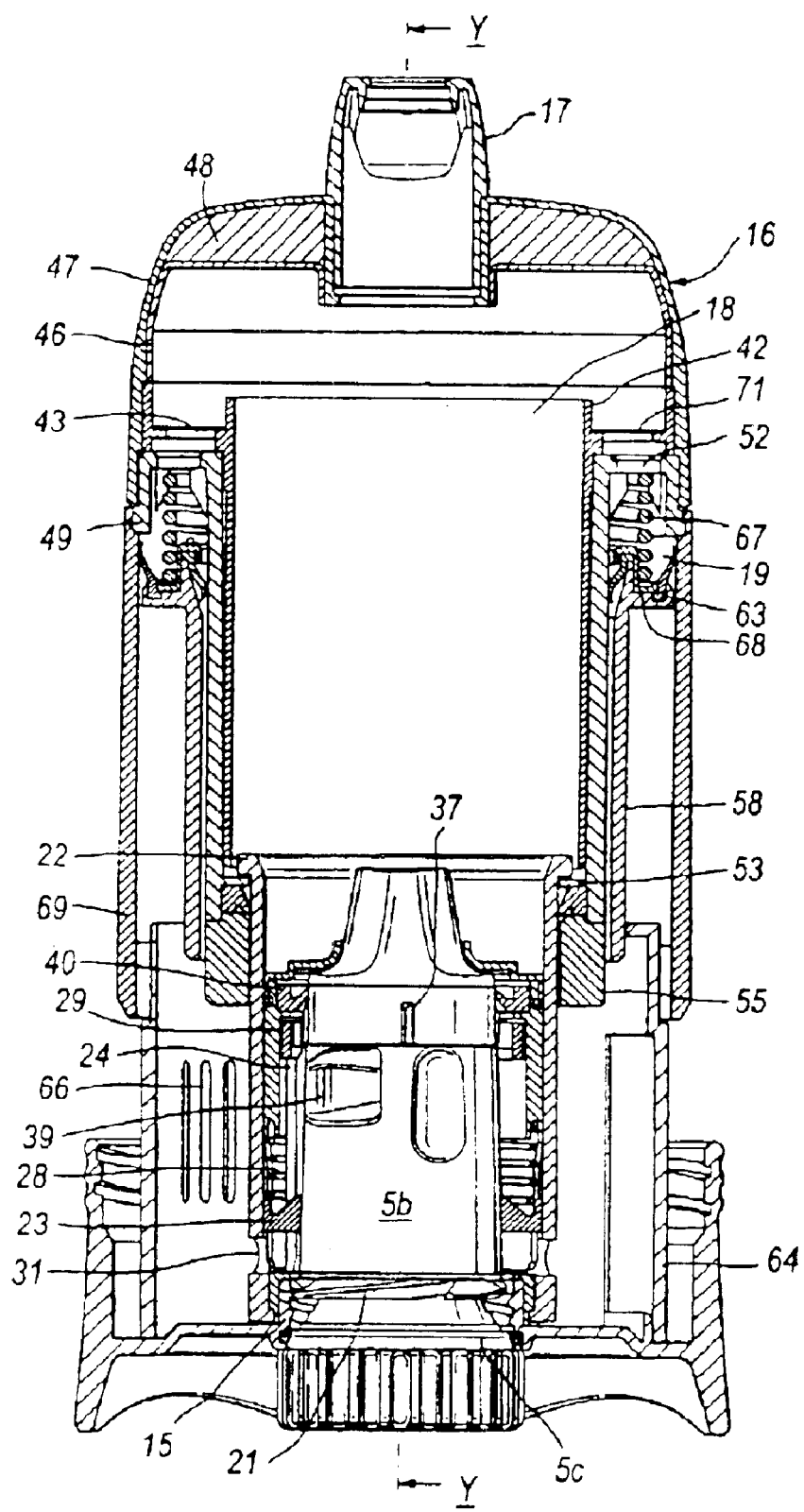
Figure 19:
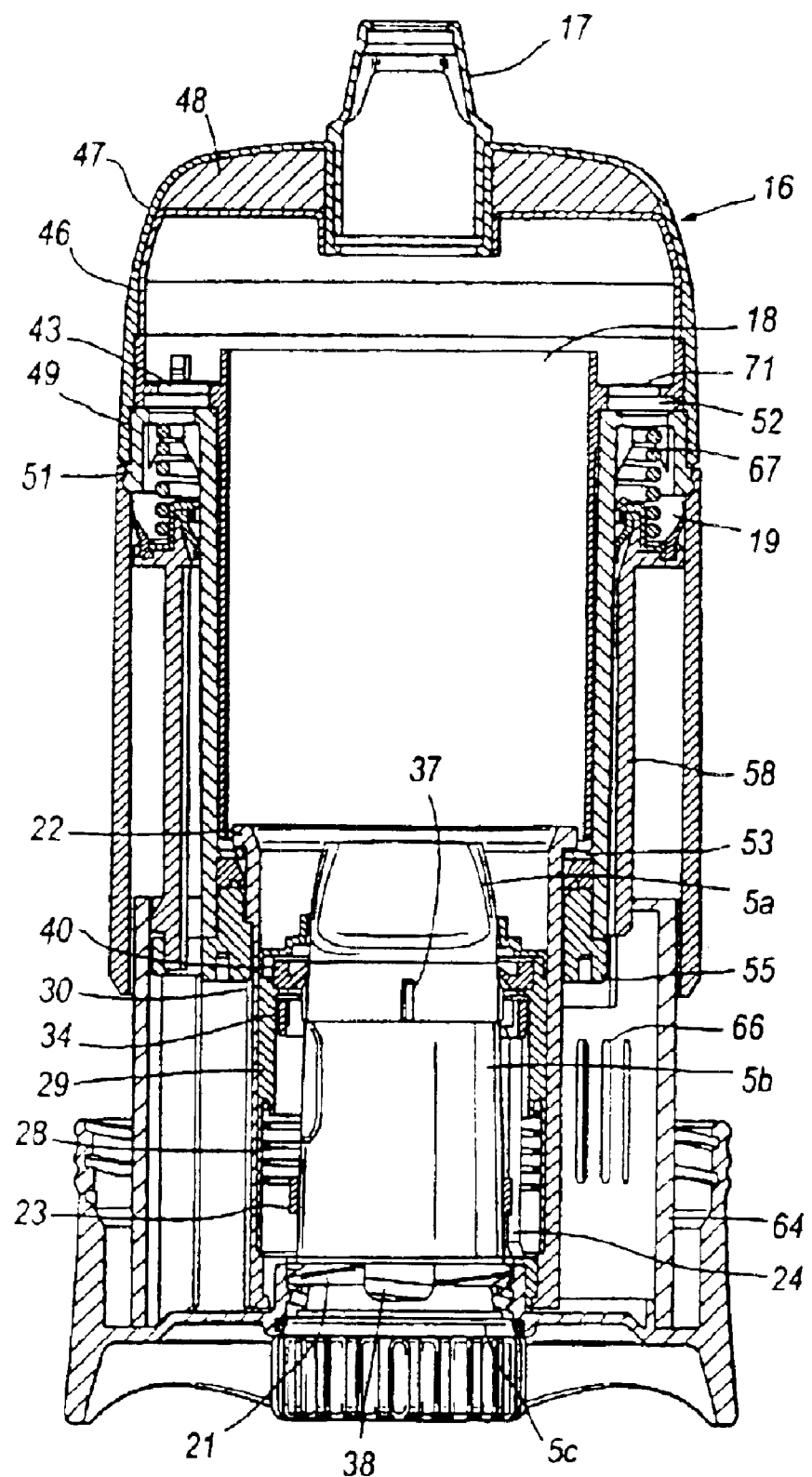
Figure 20:
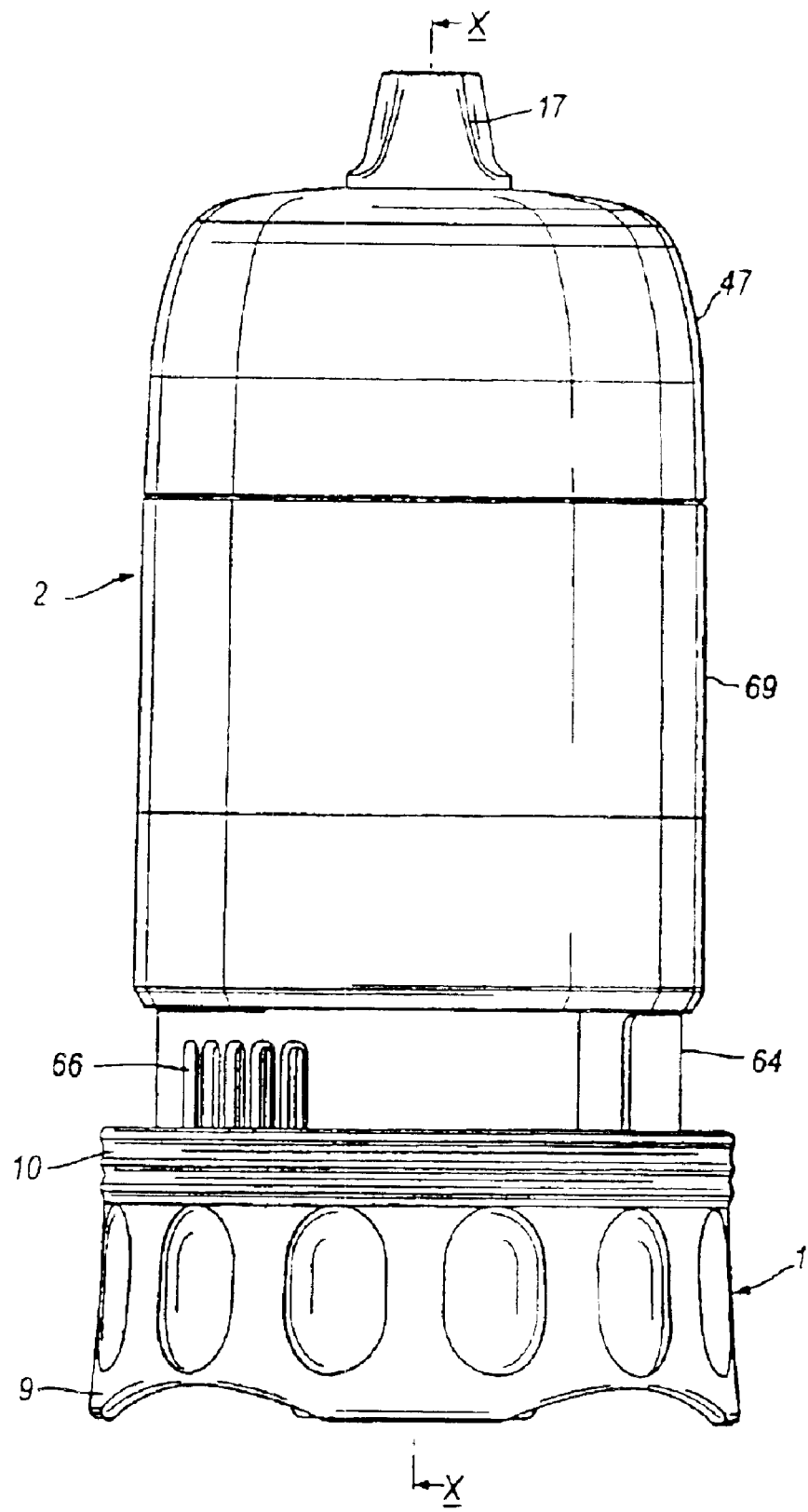
Figure 21:
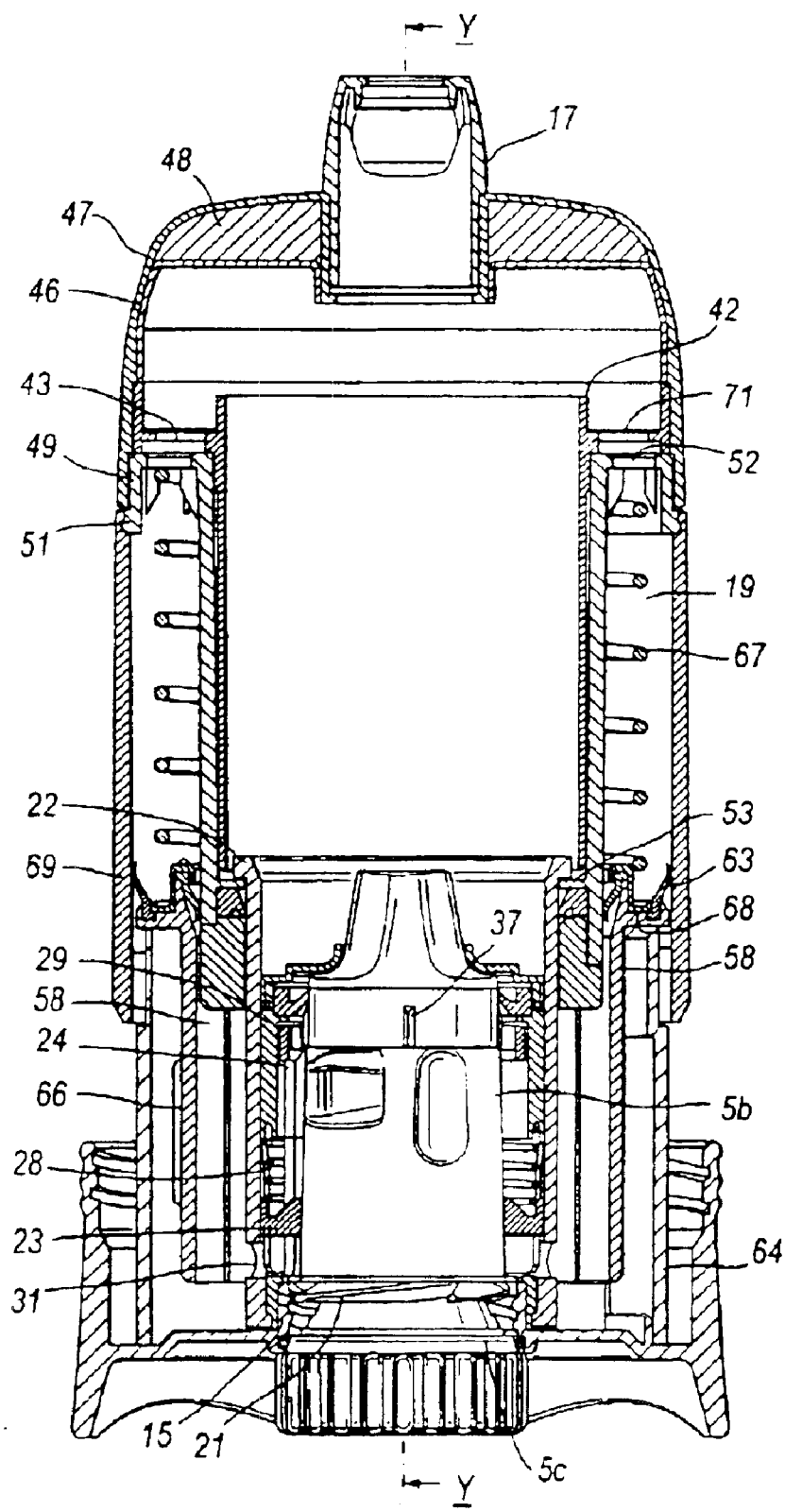
Figure 22:
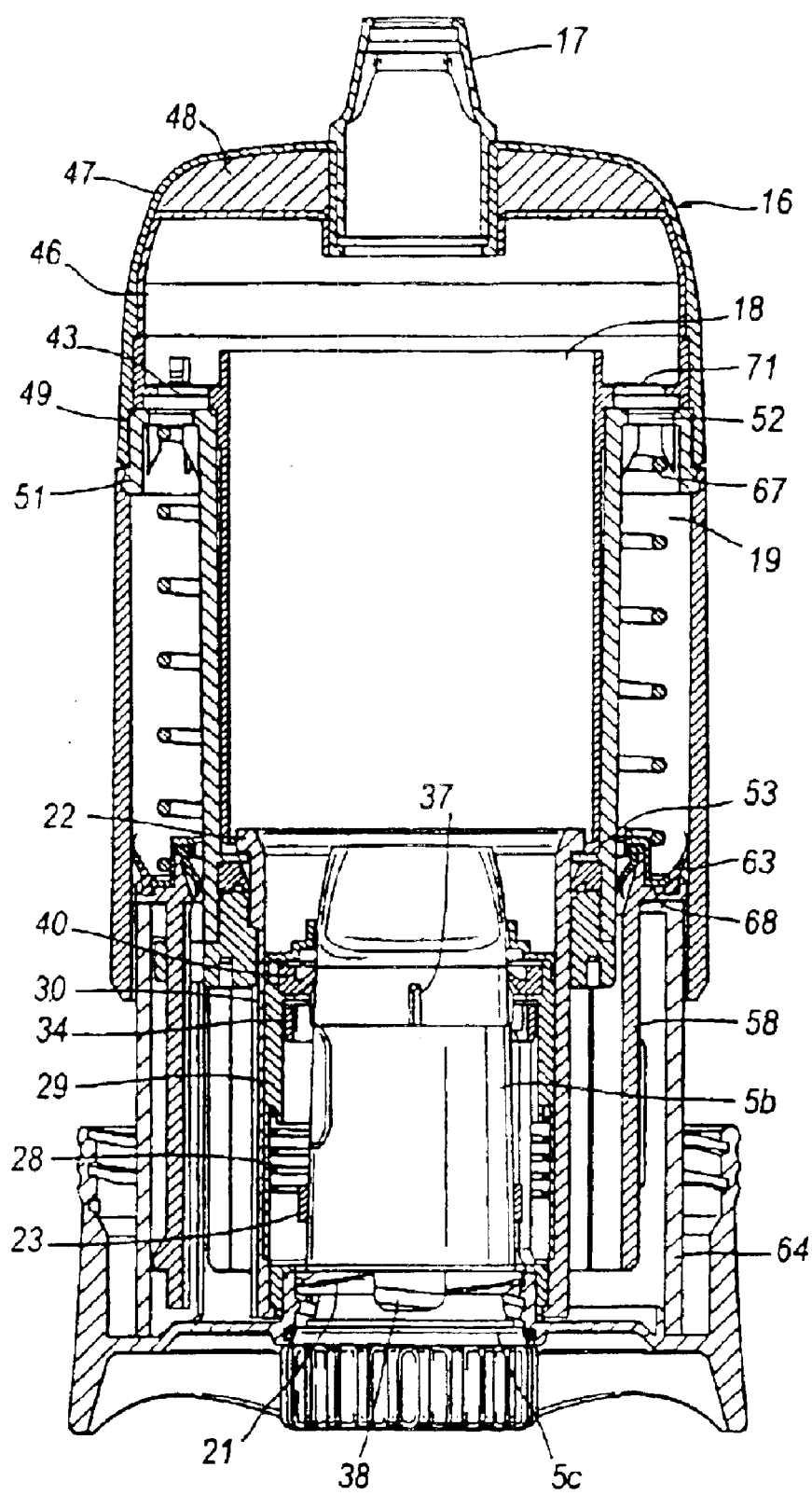
Figure 23:
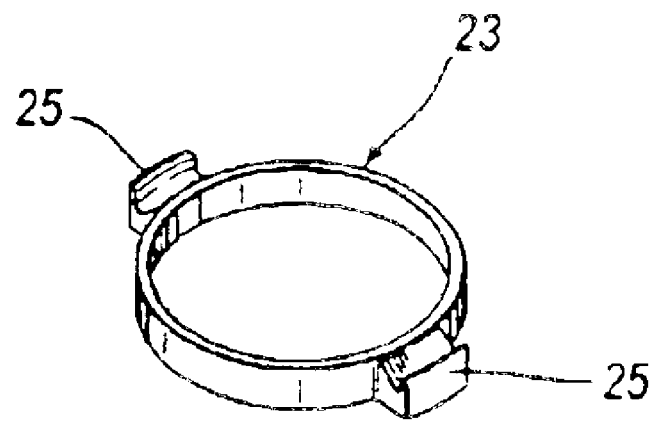
Figure 24:
Figure 25:
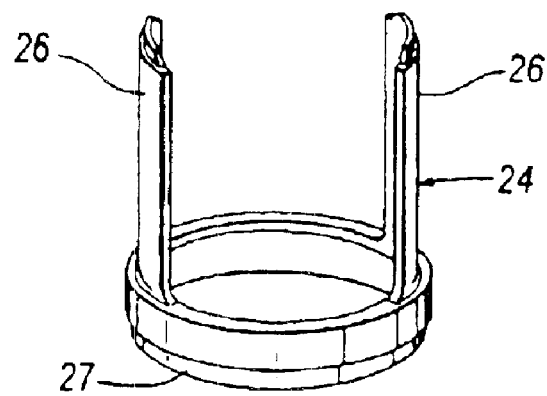
Figure 26:
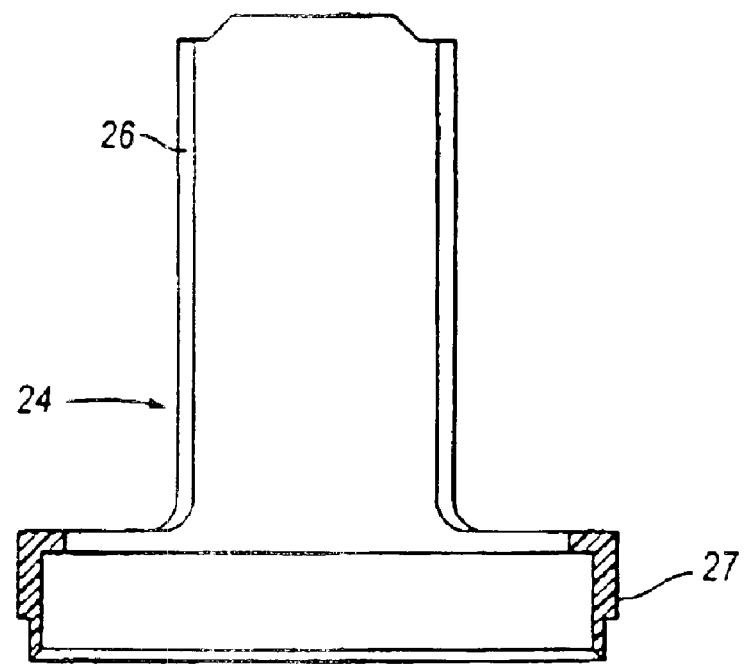
Figure 27:
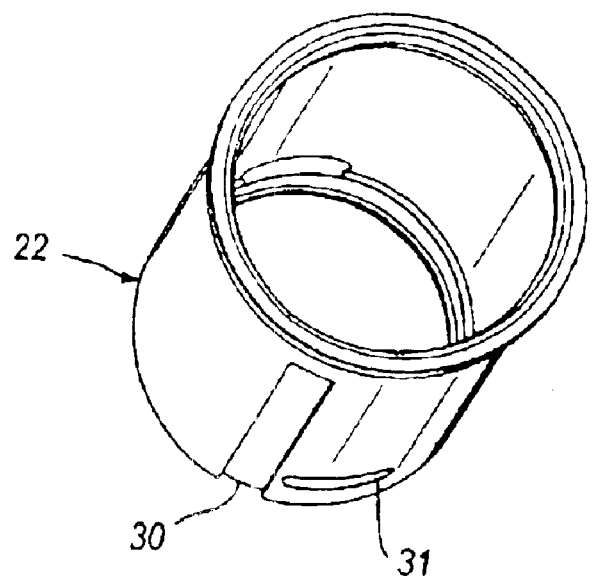
Figure 28:
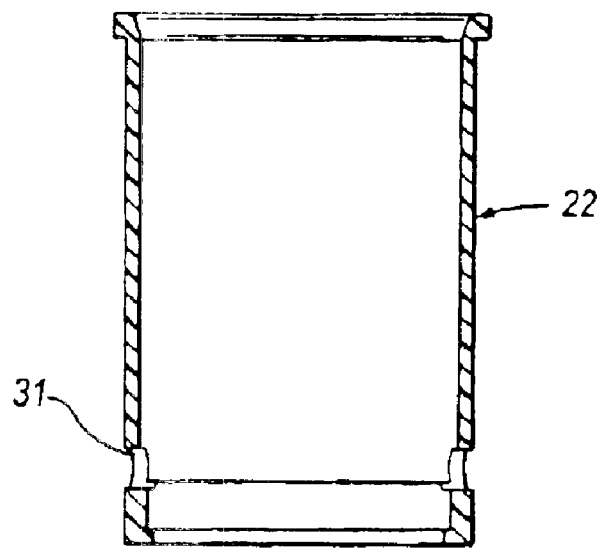
Figure 29:
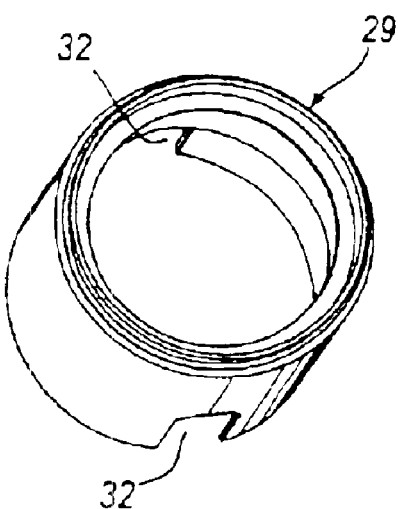
Figure 30:
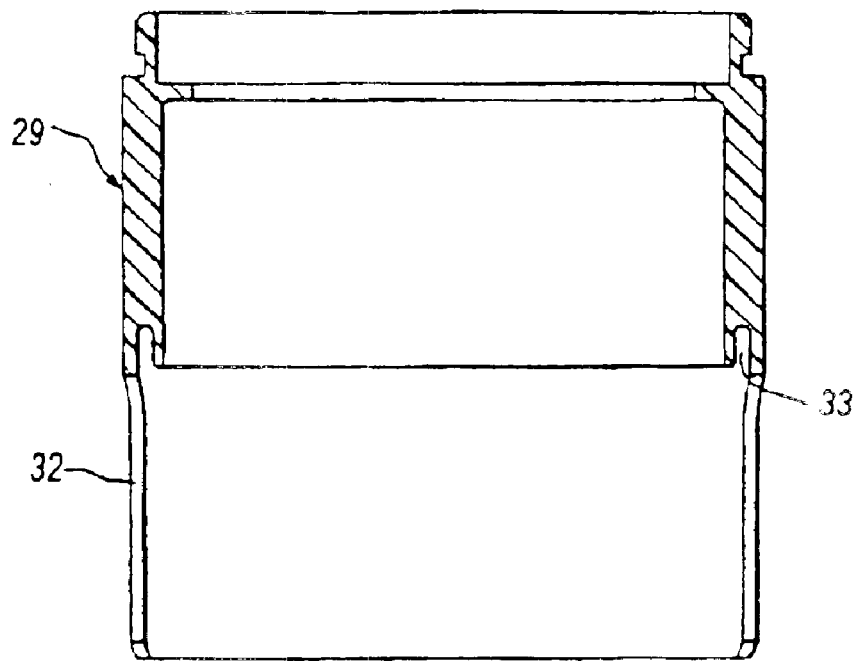
Figure 31:
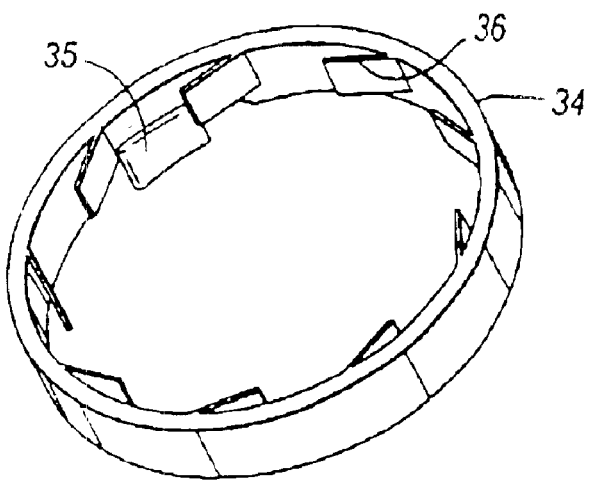
Figure 32:
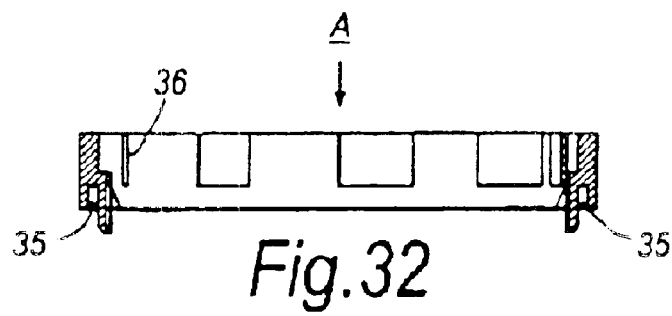
Figure 33:
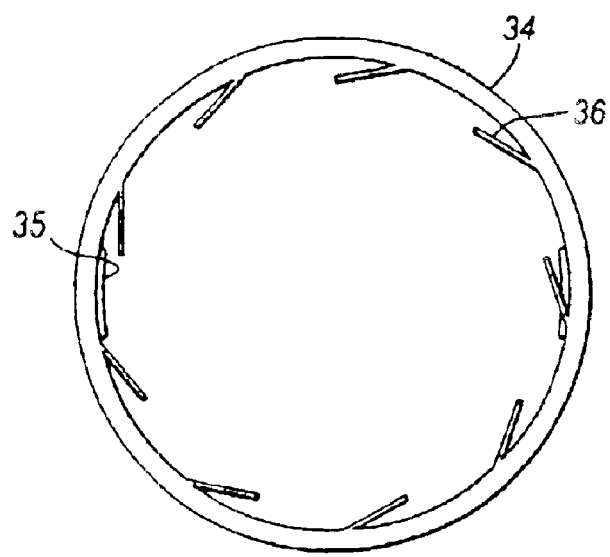
Figure 34:
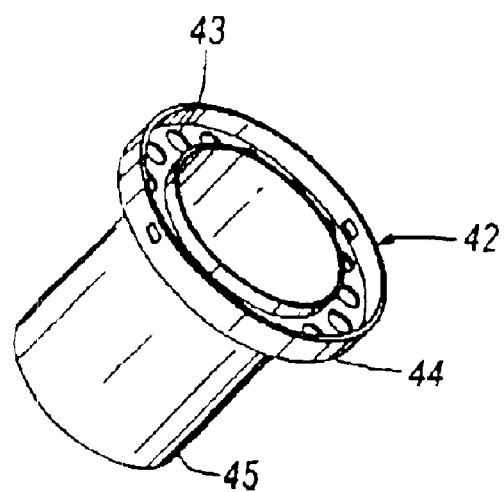
Figure 35:
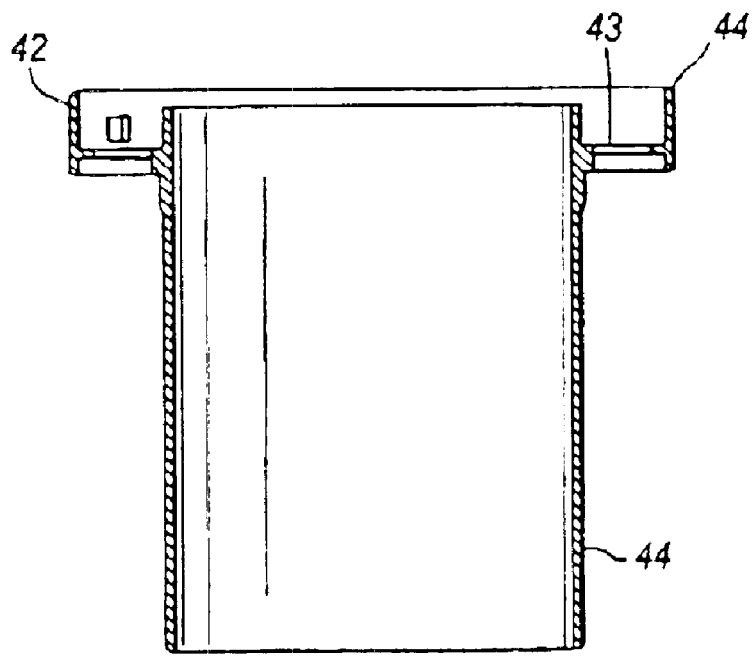
Figure 36:
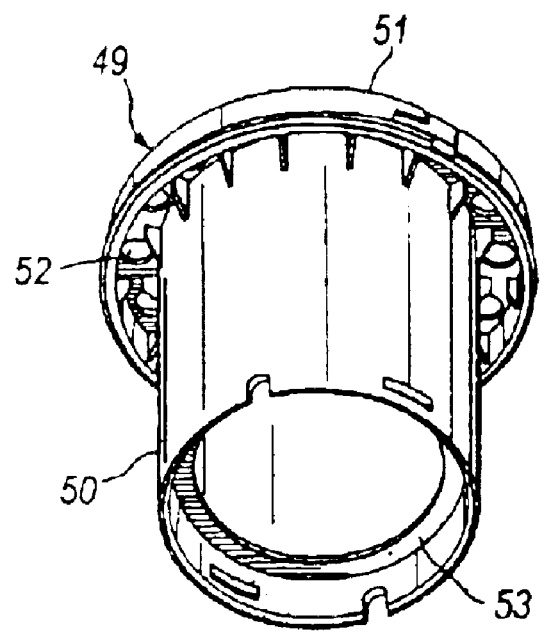
Figure 37:
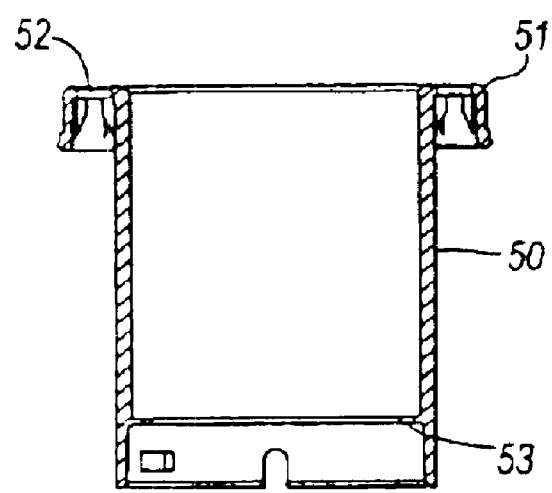
Figure 38:
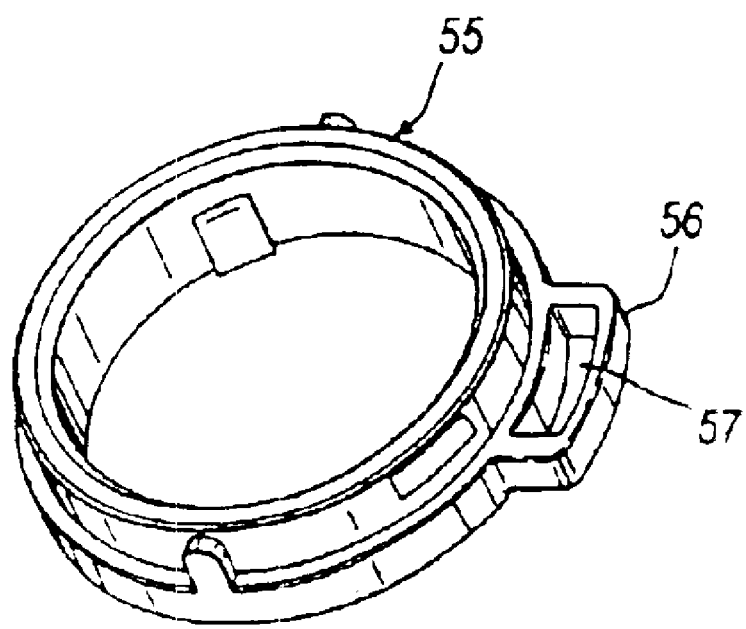
Figure 39:
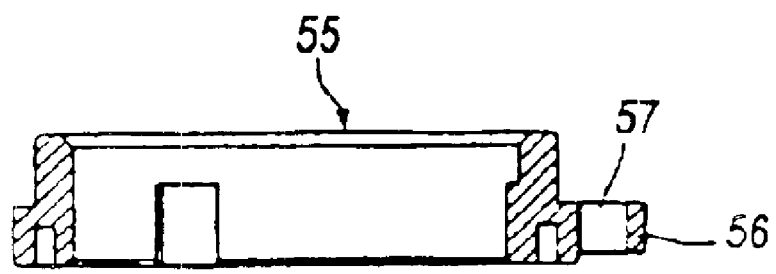
Figure 40:
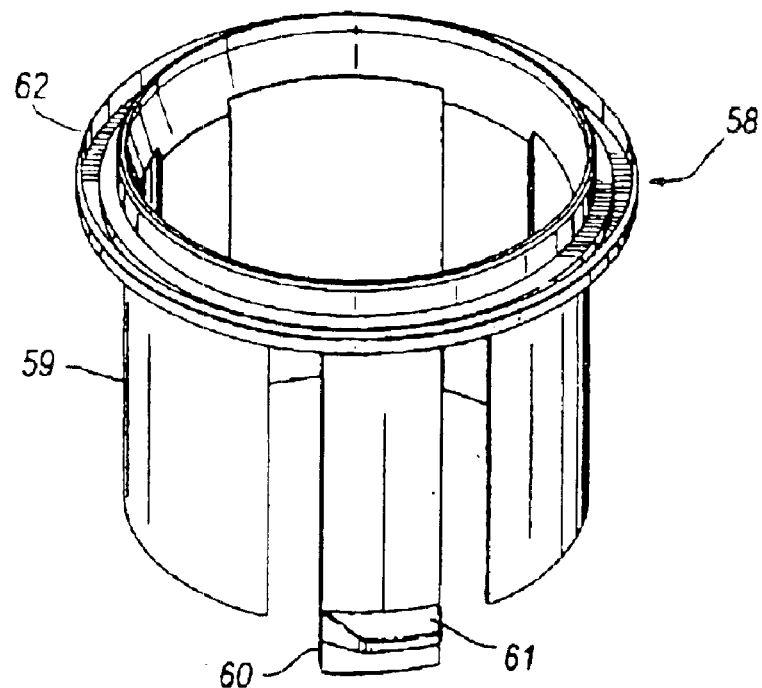
Figure 41:
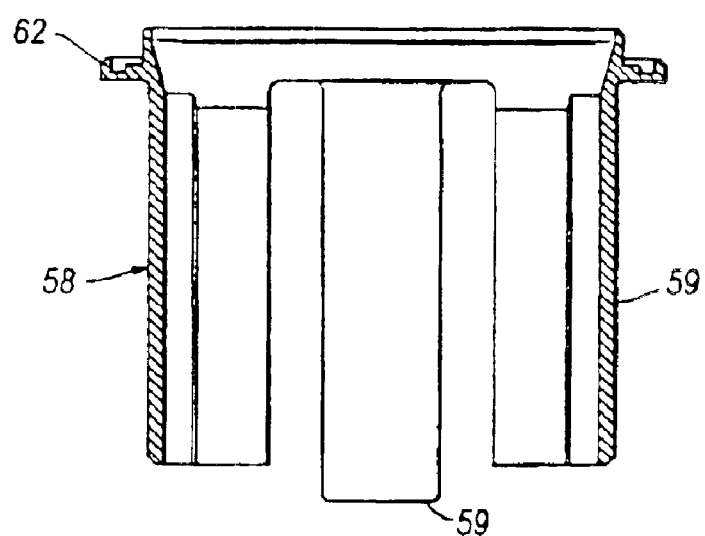
Figure 42:
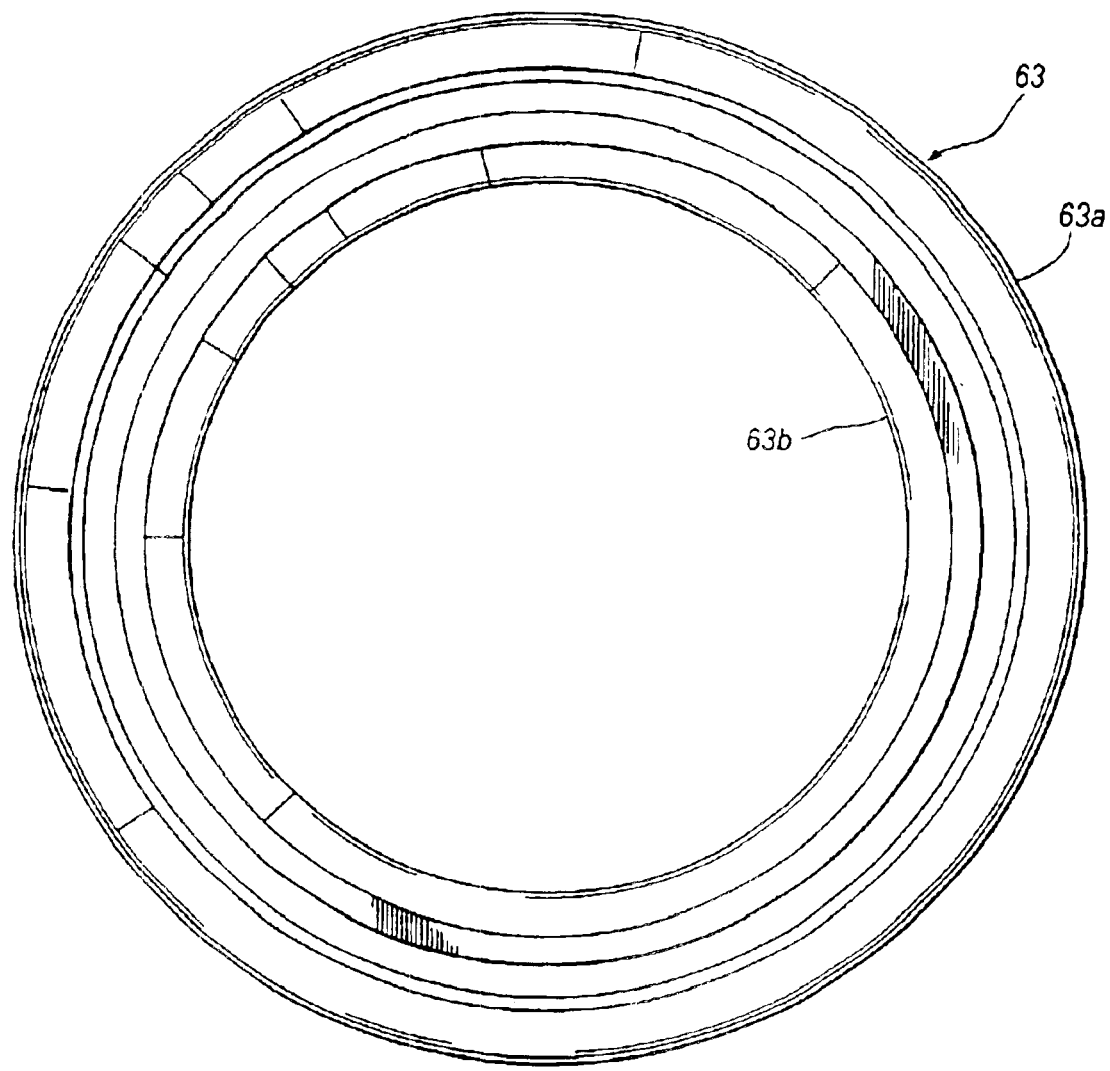
Figure 43:
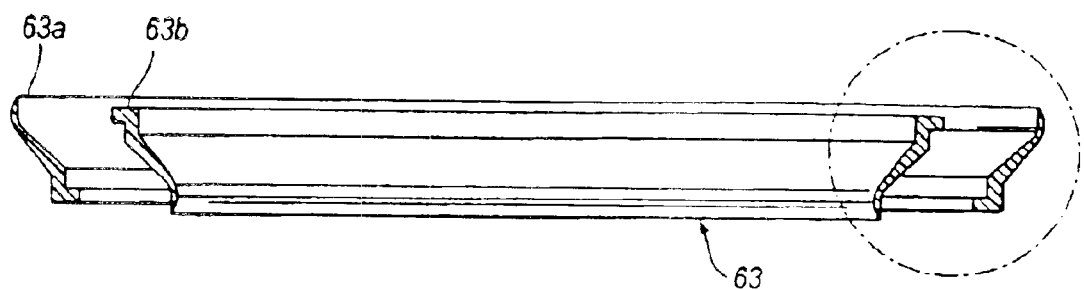
Figure 44:
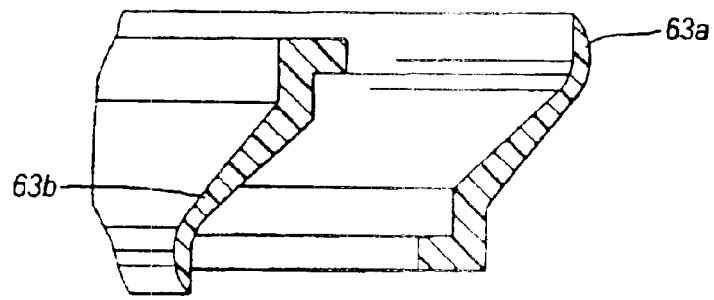
Figure 45:
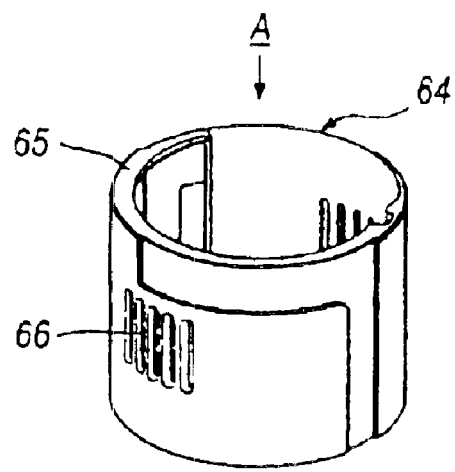
Figure 46:
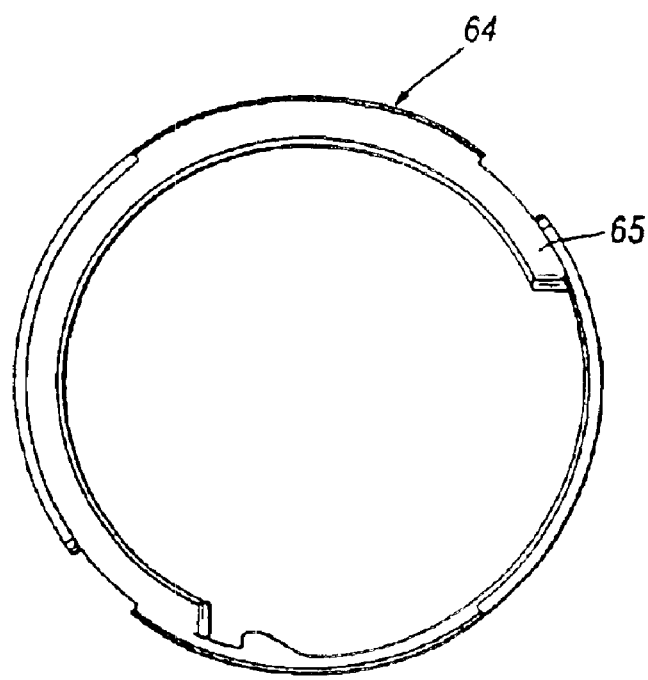
Figure 47:
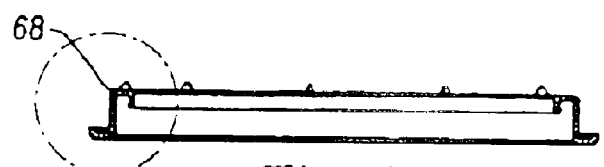
Figure 48:
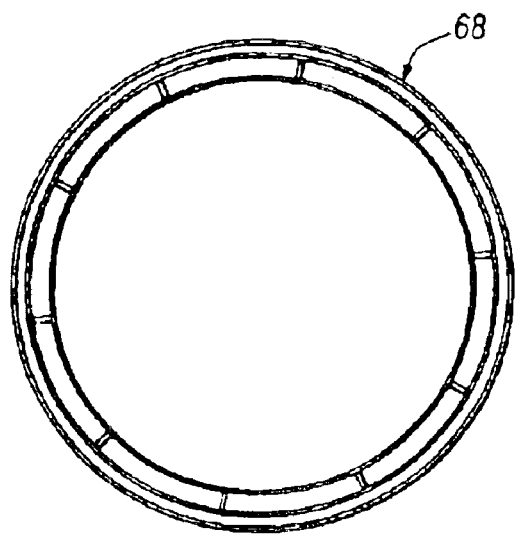
Figure 49:
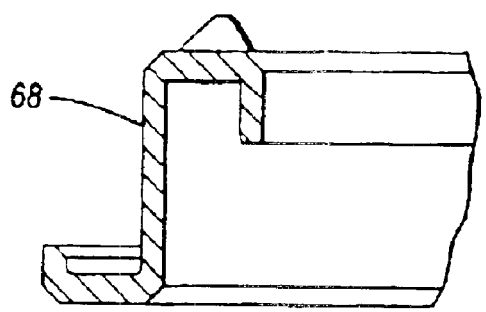

FIGS. 14, 15 and 16 correspond to the views in FIGS. 11, 12 and 13 when the body of the inhalation device is in the extended position;

FIGS. 17, 18 and 19 correspond to the views in FIGS. 14, 15 and 16 with the base rotated by a predetermined angle just prior to release of the piston;

FIGS. 20, 21 and 22 correspond to the views in FIGS. 17, 18 and 19 after the piston has been released;

FIG. 23 is a perspective view of the gripping collar;

FIG. 24 is a sectional view through the gripping collar in FIG. 23;

FIG. 25 is a perspective view of the mouthpiece drive support;

FIG. 26 is a sectional view through the mouthpiece drive support in FIG. 25;

FIG. 27 is a perspective view of the inner sleeve;

FIG. 28 is a sectional view through the inner sleeve in FIG. 27;

FIG. 29 is a perspective view of the mouthpiece seal support;

FIG. 30 is a sectional view through the mouthpiece seal support in FIG. 29;

FIG. 31 is a perspective view of the mouthpiece drive;

FIG. 32 is a sectional view through the mouthpiece drive in FIG. 31;

FIG. 33 is a view in direction A of the mouthpiece drive in FIG. 32;

FIG. 34 is a perspective view of the disposable inner sleeve;

FIG. 35 is a sectional view through the disposable inner sleeve in FIG. 34;

FIG. 36 is a perspective view of the inner piston sleeve;

FIG. 37 is a sectional view through the inner piston sleeve in FIG. 36;

FIG. 38 is a perspective view of the latch support ring;

FIG. 39 is a sectional view through the latch support ring in FIG. 38;

FIG. 40 is a perspective view of the piston;

FIG. 41 is a sectional view through the piston in FIG. 40;

FIG. 42 is a view from above of the piston seal;

FIG. 43 is a sectional view through the piston seal in FIG. 42;

FIG. 44 shows detail of the piston seal in FIG. 43;

FIG. 45 is a perspective view of the outer sleeve;

FIG. 46 is a view in direction A of the outer sleeve in FIG. 45;

FIGS. 47, 48 and 49 show different views of the piston clamp ring; and

Figure 50:
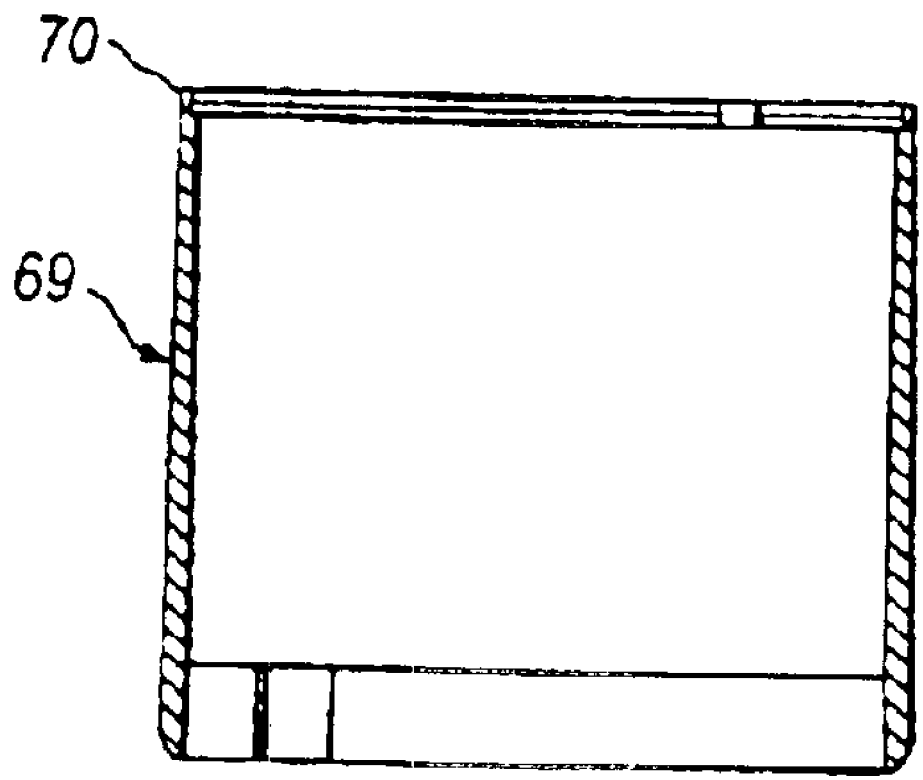

FIG. 50 is a sectional view through the external sleeve.

Figure 1:
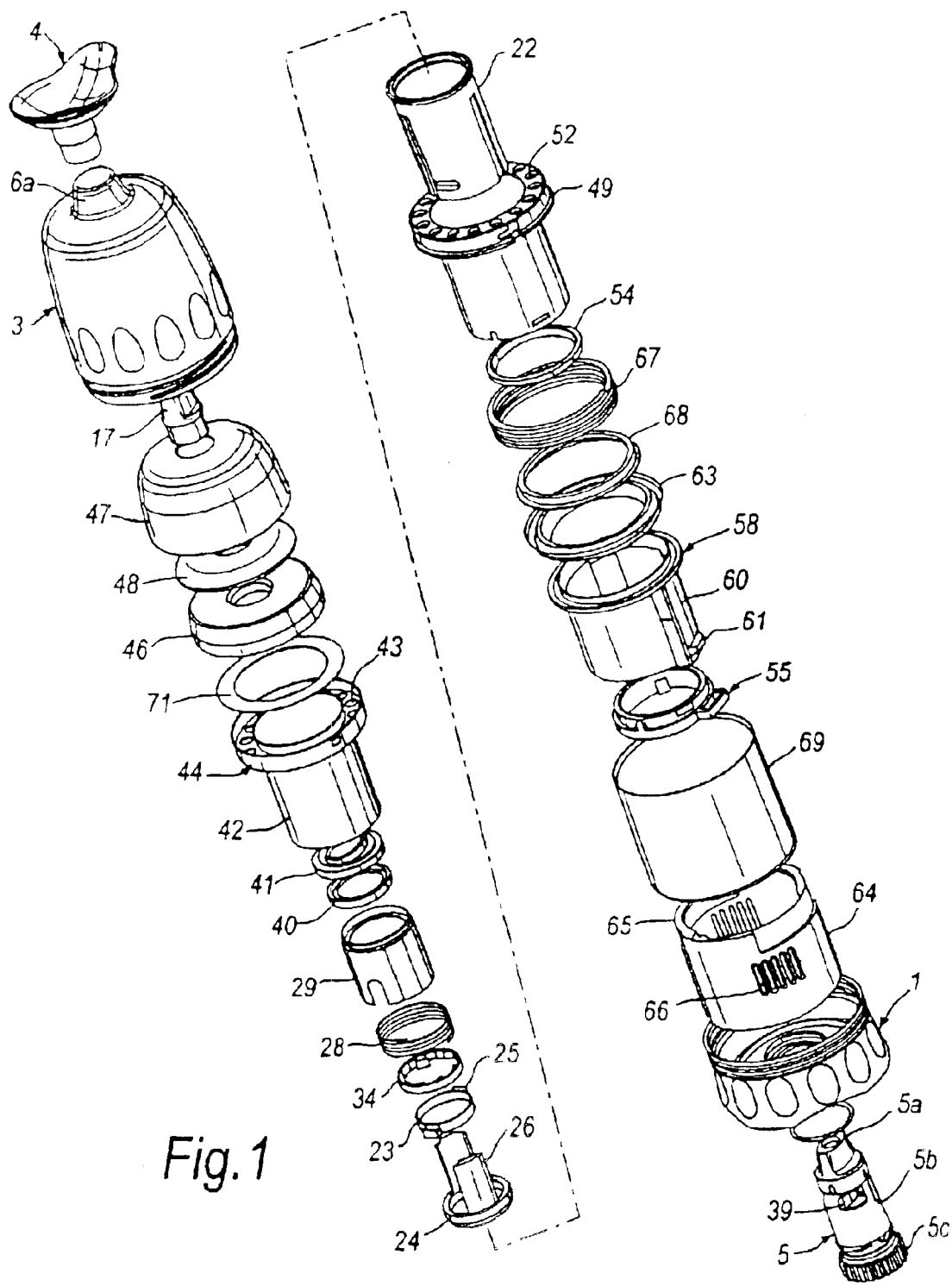
FIG. 1 is an exploded view of all the components of an inhalation device in accordance with the present invention and an inhaler.

In the exploded view in FIG. 1 and with reference to FIG. 11, the inhalation device can be seen to comprise a base 1, a body 2, a cover 3 and an optional face mask 4. An inhaler 5 suitable for use with the inhalation device can be seen beneath the base 1.

Figure 2:
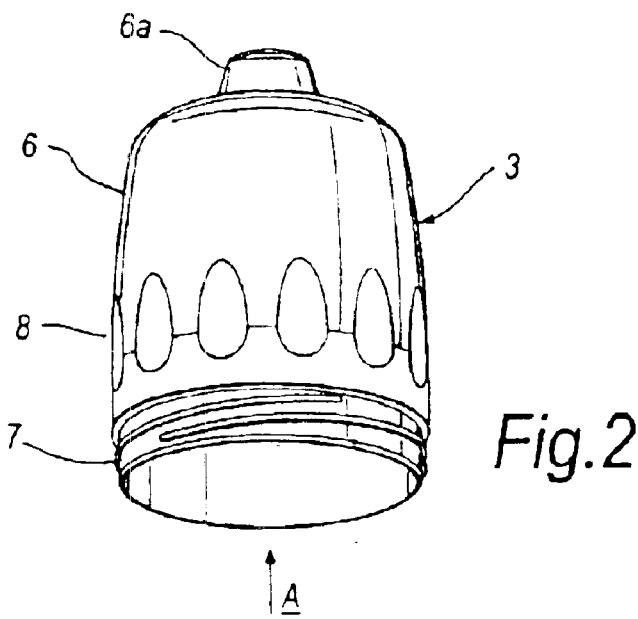
FIG. 2 is a perspective view of the cover for the inhalation device.
Figure 3:
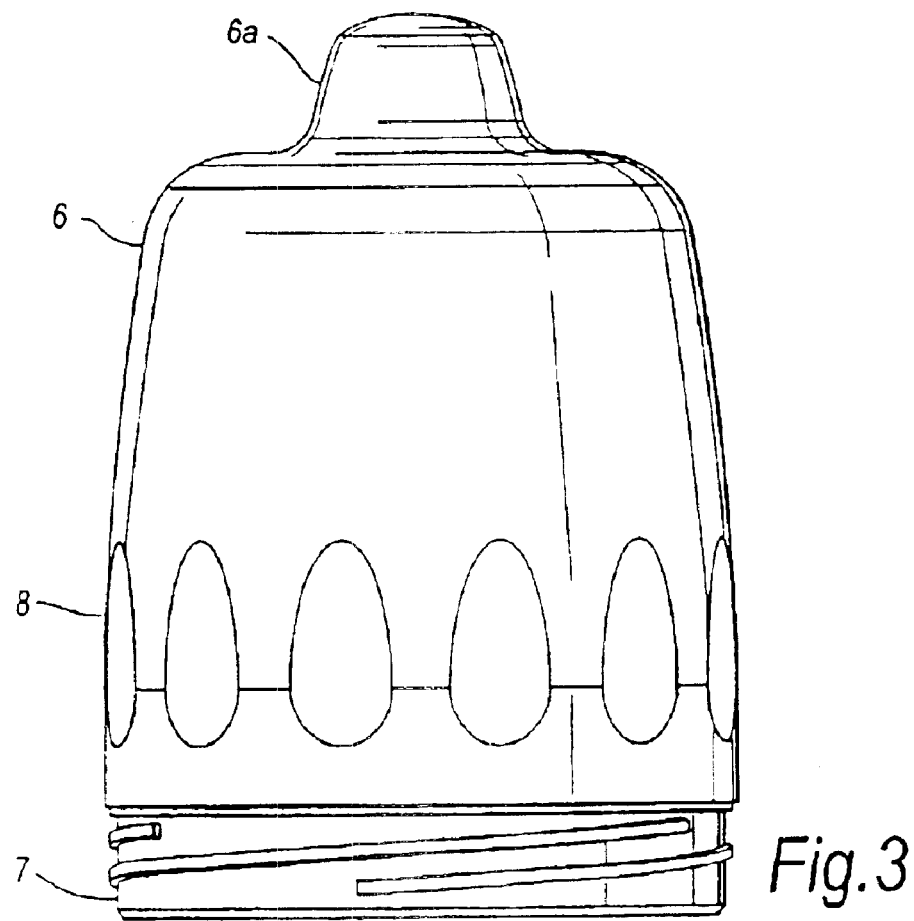
FIG. 3 is a side view of the cover in FIG. 2.

FIGS. 2 and 3 show details of the cover 3 which comprises a domed closed end 6 and a threaded open end 7. The closed end 6 is contoured to fit over the body 2 of the inhalation device (see FIG. 11). In particular, the cover 3 includes a head 6a which is contoured to fit over the mouthpiece 17 on the body 2. The cover 3 also includes a plurality of shallow recesses 8 which enable a user to grip the cover 3 to remove it from the base 1. The external configuration of the cover 3 could clearly be modified to suit different end requirements. However, the internal configuration of the cover 3 should preferably fit closely around the body 2 to avoid the presence of a large body of humid air sitting in that area of the inhalation device which would have to be addressed by increasing the volume of the desiccant disc 48 (described later).

Figure 4:
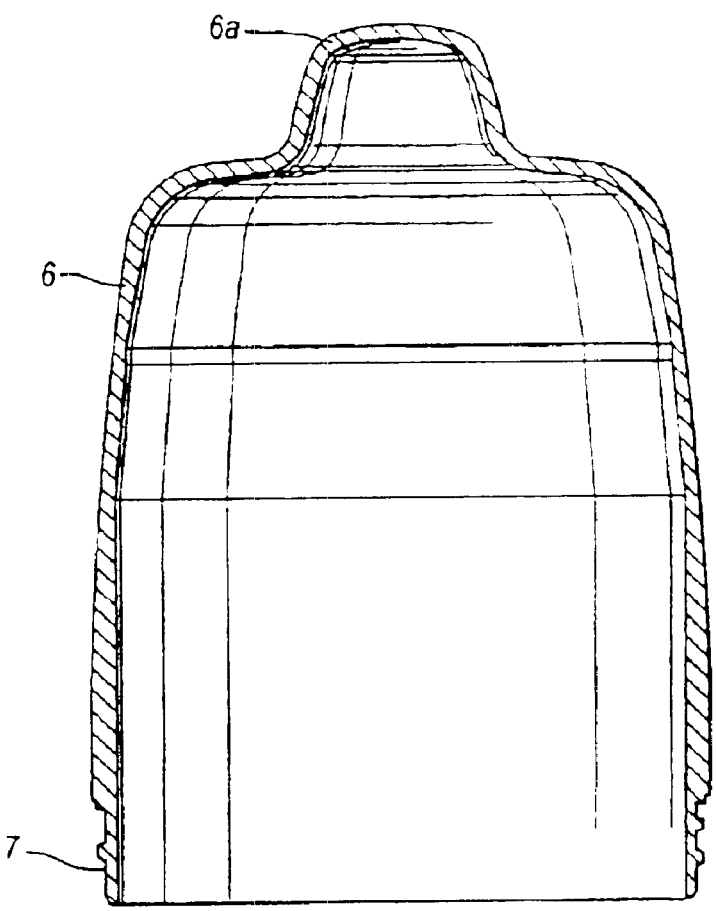
FIG. 4 is a sectional view through the cover in FIG. 3.
Figure 5:
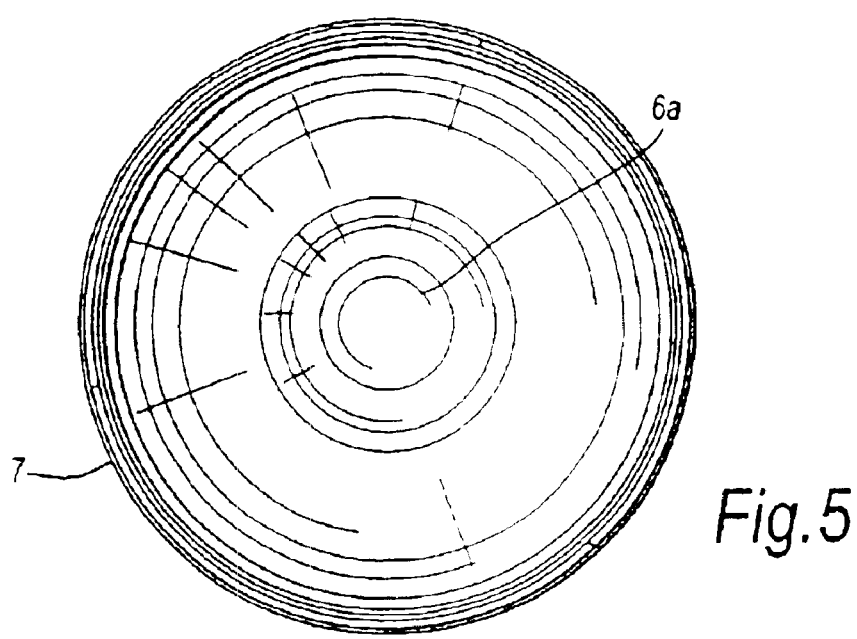
FIG. 5 is a view from below in direction A in FIG. 2 depicting the interior of cover.

FIGS. 4 and 5 are further views of the cover 3 being a sectional view and a view from below in direction A in FIG. 2 respectively.

Figure 6:
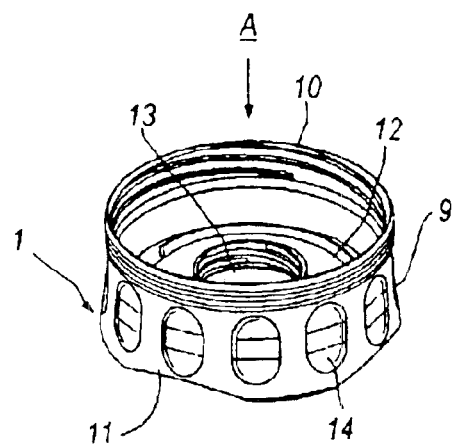
FIG. 6 is a perspective view of the base of the inhalation device.
Figure 7:
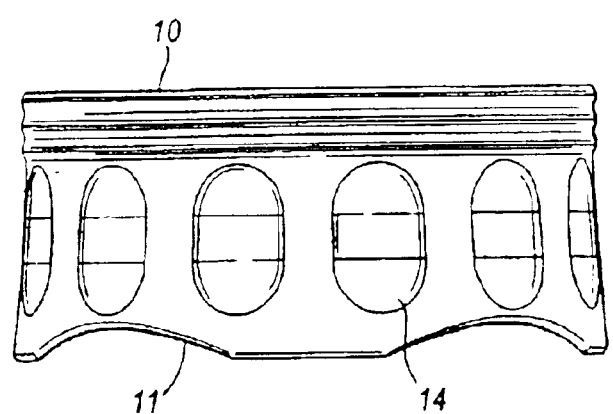
FIG. 7 is a side view of the base in FIG. 6.
Figure 8:
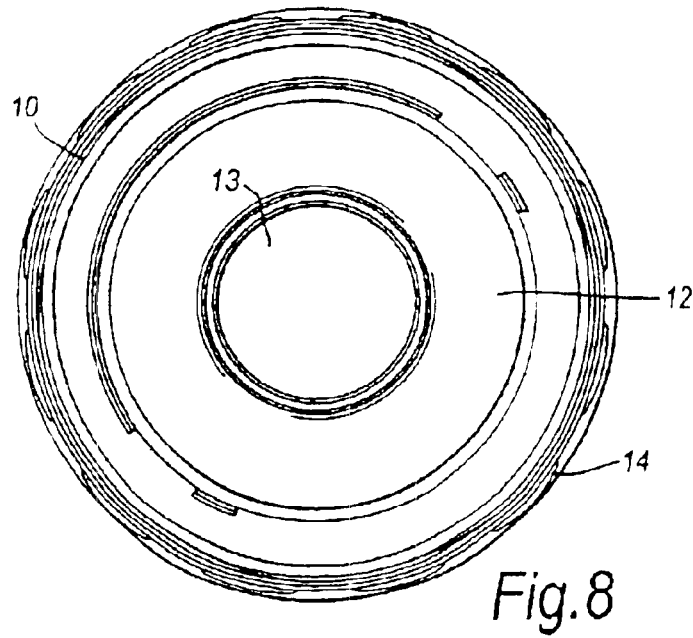
FIG. 8 is a view in direction A of the interior of the base in FIG. 6.

FIGS. 6, 7 and 8 depict the base 1 which comprises a skirt 9 with a first open end 10 which is threaded for cooperation with the threaded end 7 of the cover 3 and a second open end 11 through which the inhaler 5 (shown in FIG. 1) can be inserted into the inhalation device. A floor 12 is located at the second open end 11 with a hole 13 therethrough for insertion of the inhaler 5. The skirt 9 has a plurality of shallow recesses 14 which enable a user to grip the base 1.

Figure 9:
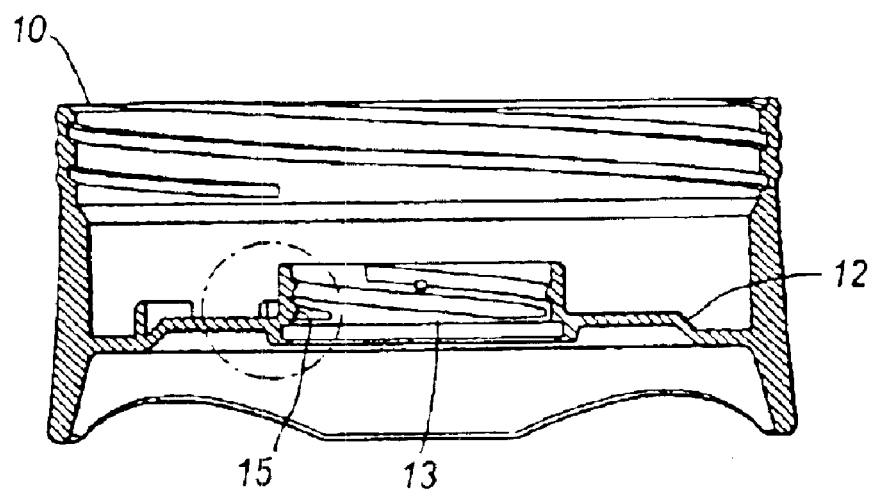
FIG. 9 is a sectional view through the base in FIG. 7.
Figure 10:
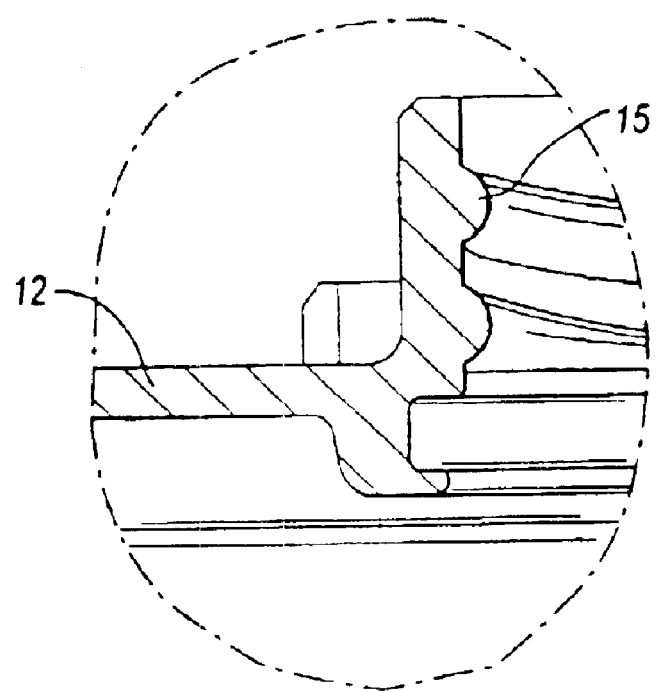
FIG. 10 shows detail of the threaded socket for an inhaler in FIG. 9.

FIG. 9 shows further detail of base 1 in cross-section. In particular, it can be seen that the hole 13 is formed with a threaded internal surface 15 which is intended to cooperate with the inhaler 5 just above the rotatable gripping part 5c depicted in FIG. 1.

FIGS. 11, 12 and 13 depict the inhalation device when assembled with the cover 3 removed. The body 2 is in the retracted position and the inhaler 5 has been inserted into the inhalation device. FIGS. 12 and 13 are sectional views in directions X—X and Y—Y through the inhalation device.

It is clear that the inhaler 5 sits centrally within the inhalation device which makes the design extremely compact. The body 2 comprises numerous elements which can be seen in the exploded view in FIG. 1. The body 2 includes an external wall 16 with a mouthpiece 17 which will sit inside the head 6a when the cover 6 is in position. There is a dispersion chamber 18 and a suction chamber 19 which are in fluid communication with each other. An annular piston 58 is moveable in the volume which comprises the suction chamber 19 and it is clear from FIGS. 12 and 21 that the piston 58 actually forms the lower moveable wall of the suction chamber 19. The dispersion chamber 18 is mounted telescopically within the suction chamber 19. Furthermore, the dispersion chamber 18 is mounted telescopically around the inhaler 5.

Preferably, the volume of dispersion chamber 18 is such that any particles dispersed in the volume will rise only to the top of the chamber and not into the volume beyond. In this way, the particles should not enter the upper volume of the body 2 and fall into the flanged rim of inner sleeve 42 (described in detail later). The inhalation device preferably includes a filter which sits in the area between the dispersion chamber 18 and suction chamber 19 to avoid particles affecting performance of the elements in the suction chamber 19. In the embodiment depicted, the filter 71 sits above the holes 43 and is in the form of a ring. A large number of filter materials could be used to form the ring. In order to avoid the particles entering the suction chamber 19, the volume of the dispersion chamber 18 must be significantly larger than the suction volume of the annular piston 58. For example, the suction volume of the piston 58 will typically be 70 ml whereas the volume of dispersion chamber 18 will typically be 200 ml. However, the volume of the dispersion chamber 18 should be minimised, if possible, in order to make the inhalation device as compact as the design will allow. Furthermore, if the volume of the dispersion chamber 18 is minimised, the inhalation device will be easier to use, requiring a smaller inhalation capacity.

In order to reduce the occurrence of particles sticking to the interior surfaces of the dispersion chamber 18, the material used for this element and other elements which make contact with the particles should comprise a polymeric material containing carbon black.

The inhaler 5 is inserted into the inhalation device from below through the base 1 whilst the body 2 is in the retracted position depicted in FIGS. 11, 12 and 13. The gripping part 5c is held in the base 1 by way of the threaded internal surface 15 which cooperates with corresponding threads 21 which are located just above the gripping part 5*c* on the inhaler 5.

The body portion 5*b* of the inhaler is held with respect to an inner sleeve 22 by a gripping collar 23. The gripping collar 23 can slide inside a mouthpiece drive support 24 which is fixed with respect to the base 1.

Reference should now be made to FIGS. 23, 24, 25 and 26 for details of the features of the gripping collar 23 and mouthpiece drive support 24.

The gripping collar 23 has two ears 25 which, when in position within the mouthpiece drive support 24 (with the inhaler 5 inserted into the device) will seat against the inner surface of the inner sleeve 22. The gripping collar 23 is forced down inside the legs 26 of the mouthpiece drive support 24 towards the annular base 27 by a spring 28. It is clear from FIG. 12 that the spring 28 will sit against the ears 25 of the gripping collar 23. The body portion 5*b* of the inhaler 5 is slightly tapered towards the mouthpiece 5*a* and accordingly, the spring 28 will push the gripping collar 23 into firm contact with the body portion 5*b*.

The spring 28 is slightly compressed between the gripping collar 23 and a mouthpiece seal support 29. The action of forcing the gripping collar 23 down the body portion 5*b* ensures that the body portion 5*b* and inner sleeve 22 cannot move with respect to each other.

For details of the inner sleeve 22 and mouthpiece seal support 29 reference should now be made to FIGS. 27, 28, 29 and 30.

The mouthpiece seal support 29 is substantially cylindrical and is fixed with respect to the inner sleeve 22 which is also substantially cylindrical. The inner sleeve 22 has three slots 30 and three holes 31 which allow air to flow through the inhalation device and into the inhaler 5 when the body 2 has been lifted to the extended position. The inner sleeve 22 is not secured in the base 1 and remains stationary if the base 1 is rotated. The inner sleeve 22 will allow the mouthpiece drive support 24 to rotate within it and, therefore, the gripping part 5c and mouthpiece 5a of the inhaler 5 will rotate with the base 1 whilst the inner sleeve 22 remains stationary and holds the body portion 5b of the inhaler 5 by way of the gripping collar 23.

The mouthpiece seal support 29 has two slots 32 and an inner rim 33. The slots 32 allow movement of the ears 25 on the gripping collar 23 when the inhaler 5 is inserted into the inhalation device. The inner rim 33 acts as a bearing surface for the spring 28 which sits between the inner rim 33 and the ears 25 on the gripping collar 23.

The rotational movement of the gripping part 5c of the inhaler 5 is linked to the rotational movement of the mouthpiece 5a of the inhaler 5 by a mouthpiece drive 34. The mouthpiece drive 34 is connected to the mouthpiece drive support 24.

Reference should now be made to FIGS. 31, 32 and 33 which show details of the mouthpiece drive 34. The mouthpiece drive support 24 has two legs 26 which slot into two recesses 35 formed in the mouthpiece drive 34. The mouthpiece drive 34 is substantially annular and has a number of flaps 36 on its interior surface which will interlock with ridges 37 on the mouthpiece 5a of the inhaler. The flaps 36 are orientated such that the mouthpiece 5a will only be driven in one direction of rotation with the gripping part 5c.

Preferably, the mouthpiece 5a is rotated at the same time as substance is released into the dosing unit of the inhaler 5, i.e. by rotating the base 1 of the inhalation device in direction R1 in FIG. 15 when the body 2 has been lifted to the extended position. After inhalation of the substance, the base 1 will then be rotated back in direction R2 but the flaps 35 will simply slip over the ridges 37 which is necessary since the mouthpiece 5a can rotate only in direction R1 with respect to the body portion 5b. Thus, the rotation of the mouthpiece 5a will result in cleaning of the interior surfaces of the inhaler 5 (for details of operation of the inhaler reference should be made to WO98/41256) only when the base 1 is rotated in direction R1.

The inhaler 5 has main inlets 38 just above the gripping part 5c and a number of bypass inlets 39 just below the mouthpiece 5a through which air can flow into the inhaler 5 to lift the substance to be inhaled from the dosing unit (not visible) within the body portion 5b.

A sealing ring 40 between the mouthpiece 5a and the mouthpiece seal support 29 prevents air from leaking into the dispersion chamber 18 rather than passing into the inhaler 5.

Preferably, the inhalation device includes a stop element 41 which is configured to ensure that only inhalers with a certain mouthpiece design can be inserted into the inhalation device. Should the inhalation device be required for use with inhalers having a large range of different mouthpieces the stop element 41 could be omitted. The stop element 41 will typically have an identical internal configuration to the mouthpiece of the inhaler which is to be inserted into the inhalation device and will rotate with the mouthpiece.

The dispersion chamber 18 lies within a disposable inner sleeve 42. For details of the disposable inner sleeve 42, reference should now be made to FIGS. 34 and 35. The disposable inner sleeve 42 comprises a substantially cylindrical body 45 with a plurality of holes 43 in a flanged rim 44 located at one end of the body.

The disposable inner sleeve 42 is connected to a disposable inner cap 46, and a disposable outer cap 47. Between the inner cap 46 and outer cap 47 is a desiccant disc 48 for drying the air within the inhalation device. It is intended that the sleeve 42 and caps 46, 47 are disposable because after repeated use of the inhalation device, particles of the substance being inhaled will collect on the interior surfaces of these elements which will eventually hamper the performance of the inhalation device.

The mouthpiece 17 of the inhalation device slots into the disposable outer cap 47 and can also be disposed of if necessary.

The disposable inner sleeve 42 slots into an inner piston sleeve 49 which can slide on the inner sleeve 22. For details of the inner piston sleeve 49 reference should be made to FIGS. 36 and 37. The inner piston sleeve 49 comprises a cylindrical body 50, having a flanged rim 51 with a plurality of holes 52 at one end. The other end of the cylindrical body 50 includes an inner rim 53 which bears on the outer surface of inner sleeve 22.

There is an inner seal 54 which sits against the rim 53 inside the inner piston sleeve 49. Below the inner seal 54 is a latch support ring 55. For details of the latch support ring 55 reference should be made to FIGS. 38 and 39. The latch support ring 52 comprises a lip 56 with a slot 57 therethrough.

A piston 58 is located adjacent to the latch support ring 55 and is moveable with the inner piston sleeve 49. For details of the piston 58 reference should now be made to FIGS. 40 and 41. The piston 58 has a substantially cylindrical body 59 with a latch 60. The latch 60 is in the form of a leg with a flange 61. The piston 58 also comprises an annular flange 62 in which a piston seal 63 sits. Reference should now be made to FIGS. 42, 43 and 44 for details of the piston seal 63. The piston seal 63 is constructed from an outer ring 63a and an inner ring 63b. Preferably, the inner ring 63b forms the leading edge of the seal when the piston 58 fires (see FIGS. 21 and 22) and the outer ring 63a forms the trailing edge. The piston seal 63 should be manufactured to suit the sliding motion of the piston 58, i.e. not too tight since movement will be affected and not too loose otherwise there will be decreased suction in the suction chamber 19 if the seal leaks.

For manufacturing purposes, the outer ring 63a and inner ring 63b can be connected by spaced thin connecting bridges or strips to facilitate injection moulding of the parts.

In the retracted position of the body 2, the piston 58 sits adjacent to the latch support ring 55 with the flange 61 on latch 60 resting against the lip 56 on the latch support ring 55. When the body 2 is lifted to the extended position shown in FIG. 16, the piston 58 and latch support ring 55 move with the inner sleeve 42 and inner piston sleeve 49.

A transparent outer sleeve 64 which is fixed to the base 1 cooperates with the piston 58. The piston 58 can slide with respect to the outer sleeve 64 from the retracted position (FIGS. 12 and 13) to the extended position (FIGS. 15 and 16). Reference should now be made to FIGS. 45 and 46 which show details of the outer sleeve 64. The outer sleeve 64 is substantially cylindrical but has a cam surface 65 on its inner surface. The cam surface 65 cooperates with the outer surface of piston 58 when the piston is in the extended position in FIG. 16. When the base 1 is rotated to prime the inhalation device for use (FIGS. 17, 18 and 19 and FIGS. 20, 21 and 22) the cam surface 65 will eventually push the latch 60 through the hole 57 in the lip 56 on the latch support ring 55. At this point, the piston 58 will be forced downwardly through the latch support ring 55 by a spring 67 which sits between the inner piston sleeve 49 and the piston 58. The volume of the suction chamber 19 will increase on release of the piston 58 and draw air from the dispersion chamber 18 through the holes 43 and 52 in the inner sleeve 42 and inner piston sleeve 49. A negative pressure will then be created in the dispersion chamber 18.

The outer sleeve 64 has a number of air vents 66 which allow air to be drawn in from outside the inhalation device when the piston 58 is released and accordingly, an airflow is created through the inhaler 5 as a result of the negative pressure in the dispersion chamber 18.

A piston clamp ring 68 is located between the piston seal 63 and spring 67 which serves to clamp the piston seal 63 on the piston 58 within the annular flange 62. Reference should now be made to FIGS. 47, 48 and 49 for details of the profile of piston clamp ring 68.

The external sleeve 69 forms part of the external surface of the body 2 of the inhalation device. Details of the external sleeve 69 can be seen in FIG. 50. The external sleeve 69 has a threaded end 70 which threads into the outer cap 47. In this way, the disposable outer cap 47, disposable inner cap 46, disposable inner sleeve 42 and the desiccant disc 48 can be removed and replaced. The external sleeve 69 slides over the external surface of the outer sleeve 64.

The actuation of the inhalation device will now be described with reference to FIGS. 11 to 22.

FIGS. 11, 12 and 13 show various views of the inhalation device when the body is in the retracted (or rest) position and an inhaler 5 has been inserted through the base 1.

In FIGS. 14, 15 and 16, the body 2 has been lifted away from the base 1 to the extended position. In FIGS. 15 and 16 it can be seen that the inhaler 5 (which is held by the base 1) remains stationary whilst the disposable inner sleeve 42, the inner piston sleeve 49, the piston 58 and the latch support ring 55 move upwards with the body 2. The lifting of the body 2 reveals the air vents 66 in the outer sleeve 64 which will allow air to flow into the inhalation device.

In FIGS. 17, 18 and 19, the base 1 has been rotated with respect to the body 2. In these Figures the inhalation device is shown just prior to the piston 58 being released. When the base 1 is rotated, the gripping part 5c and mouthpiece 5a of the inhaler 5 rotate simultaneously. This is achieved as a result of the connection between the mouthpiece drive support 24 and the mouthpiece drive 34 which link the gripping part 5c and mouthpiece 5a rotationally when the base 1 is rotated in direction R1. In this way, the interior surfaces of the inhaler 5 can be cleaned by the scraping elements actuated by the rotation of the mouthpiece 5a prior to each use. The inner sleeve 22 does not rotate with the base 1 and, therefore, the body portion 5b of the inhaler 5 is held by the gripping collar 23 whilst the gripping part 5c and mouthpiece 5a rotate.

In FIGS. 20, 21 and 22 the piston 58 has been released drawing air into the inhalation device by the creation of a negative pressure in the dispersion chamber 18. The piston 58 is held by the latch support ring 55 during rotation of the base 1 until the cam surface 65 on the interior of the outer sleeve 64 makes contact with the latch 60 on the piston. At this point the flange 61 is pushed inwardly and slips through the hole 57 in the lip 56 on the latch support ring 55. It can be seen from FIG. 46 that the base 1 can rotate by a predetermined angle without the cam surface 65 contacting the latch 60, this angle being sufficient to prime the inhaler 5 for use to release the substance into a dosing unit ready for inhalation. When the piston 58 is released air will flow through the air vents 66, the air slots 30 and air holes 31 in the inner sleeve 22 and pass into the main inlets 38 and by-pass inlets 39 in the inhaler 5. The airflow will lift the substance to be inhaled into the dispersion chamber 18 ready for inhalation.

When the user has inhaled, the base 1 should be rotated back in direction R2. This will cause the gripping part 5c to rotate also and ensure that the inhaler 5 is returned to a position ready for subsequent use. The mouthpiece 5a will not rotate in direction R2 with respect to the body portion 5b and this has been taken into account by provision of the flaps 36 inside the mouthpiece drive 34 which will only engage the mouthpiece 5a in direction R1. After rotation in direction R2, the body 2 should be pushed back down towards the base 1 which will result in the latch 60 on the piston 58 passing back through the latch support ring 55 ready for subsequent actuation.

The cover 3 should be replaced after use to ensure that the contents of the inhalation device are maintained as dry as possible. A desiccant disc 48 is located in the cavity between the inner cap 46 and outer cap 47 which can be replaced when necessary. The drying agent can take many forms but the desiccant disc 48 is very practical for this purpose. In order to encourage the user to replace the cover 3, the outer surfaces of the cover 3 and base 1 can be decorated with an artwork comprising two parts which is only made complete by securing the cover 3 in position over the base 1. Alternatively, an audible alarm can be located on the base 1 of the inhalation device which is actuated after a delay period which is sufficient to allow the user to actuate the inhalation device.

Whilst the preferred embodiment of the inhalation device includes the stop element 41 to ensure that the inhalation device works only with certain inhalers, the stop element 41 could be omitted allowing use with any inhaler having the same configuration of gripping part 5c. Furthermore, the mouthpiece drive support 24 and mouthpiece drive 34 could be omitted should the inhalation device be required for use with an inhaler which has a rotatable gripping part 5c but the mouthpiece 5a does not need to be rotated.

The inhalation device described and depicted herein has significant advantages over prior art devices by virtue of its compact design, increased performance characteristics and the fact that it is able to work with inhalers which incorporate an internal scraping element.

What is claimed is:

1. An inhalation device for use with an inhaler comprising a dispersion chamber constructed for fluid communication with the inhaler, a suction chamber in fluid communication with the dispersion chamber, and mounting structure to telescopically mount the dispersion chamber when in use on the inhaler for movement between an inactive position in which the dispersion chamber surrounds the inhaler and an active position telescopically displaced from the inhaler, the suction chamber being constructed to enable the internal volume of said suction chamber to be increased during use which produces a negative pressure in said dispersion chamber thereby drawing a substance to be inhaled from the inhaler into the dispersion chamber for subsequent inhalation.

2. An inhalation device as claimed in claim 1, wherein a piston is moveable within the suction chamber.

3. An inhalation device as claimed in claim 2, wherein the piston has an annular construction.

4. An inhalation device as claimed in claim 3, wherein the piston carries an annular seal member.

5. An inhalation device as claimed in claim 4, wherein the annular seal member comprises inner and outer coaxial annular seals.

6. An inhalation device as claimed in claim 1, further comprising a filter between the dispersion chamber and suction chamber to prevent the disperse substance from entering the suction chamber.

7. An inhalation device as claimed in claim 2, wherein the dispersion chamber is mounted telescopically within the suction chamber.

8. An inhalation device as claimed in claim 7, where the piston is releasably connected adjacent to and moveable with the dispersion chamber which is moveable between a retracted position, where it surrounds the inhaler, to an extended position, where it sits substantially above the inhaler.

9. An inhalation device as claimed in claim 8, wherein the device further comprises a releasing mechanism for releasing the piston from the dispersion chamber and a biasing means for biasing the piston away from the dispersion chamber when in the extended position and the device is primed for use.

10. An inhalation device as claimed in claim 9, wherein when the piston is released the movement of the piston within the suction chamber creates a negative pressure in the dispersion chamber thereby drawing air through the inhaler.

11. An inhalation device as claimed in claim 1, wherein the inhalation device comprises a base and a body and is primed for use by lifting the body away from the base and then rotating the base with respect to the body.

12. An inhalation device as claimed in claim 11, wherein the dispersion chamber is located in the body and the inhaler is held in the base.

13. An inhalation device as claimed in claim 12, wherein the inhaler has a mouthpiece, a body portion and a rotatable gripping part.

14. An inhalation device as claimed in claim 13, wherein when the inhaler is located within the inhalation device, the rotatable gripping part is held in the base of the inhalation device so that the rotation of the base causes rotation of the rotatable gripping part.

15. An inhalation device as claimed in claim 14, wherein the rotation of the gripping part of the inhaler causes the substance to move into a release position within the body portion of the inhaler.

16. An inhalation device as claimed in claim 13, wherein the inhaler mouthpiece is rotatable having a scraping means acting on its interior surfaces which cleans the inhaler prior to each use.

17. An inhalation device as claimed in claim 16, wherein the inhalation device further comprises a connecting means which links the rotational movement of the gripping part of the inhaler to the rotational movement of the mouthpiece of inhaler such that rotation of the base in one direction results in the cleaning of the interior surfaces of the inhaler.

18. An inhalation device as claimed in claim 13, wherein the inhalation device further comprises a clamping means which holds the body portion of the inhaler whilst allowing the gripping part to rotate with the base.

19. An inhalation device as claimed in claim 11, wherein the body of the inhalation device further comprises a means for drying the air contained within the device and the substance to be inhaled.

20. An inhalation device as claimed in claim 11, wherein the body of the inhalation device further comprises a number of separable elements which can be replaced after a predetermined number of uses.

21. An inhalation device as claimed in claim 1, wherein the inhalation device comprises a stop element which is configured to ensure that only certain inhalers can be inserted into the device.

22. An inhalation device as claimed in claim 1, further comprising a cover which at least partially encases the inhalation device when not in use.

23. An inhalation device as claimed in claim 22, wherein the cover seals and encases the body of the device and connects with the base of the device.

24. An inhalation device as claimed in claim 23, wherein the cover and base include parts of an artwork which is only made complete when the user has replaced the cover on the base thereby ensuring that the contents of the inhalation device are sealed within.

25. An inhalation device as claimed in claim 22, wherein the inhalation device comprises an audible alarm which is activated after a given period of time should the cover not be replaced.

* * * * *